(12) United States Patent
Graf et al.

(10) Patent No.: US 8,527,250 B2
(45) Date of Patent: Sep. 3, 2013

(54) METHOD AND APPARATUS FOR ASSESSING FEASIBILITY OF PROBES AND BIOMARKERS

(75) Inventors: John Frederick Graf, Ballston Lake, NY (US); Brion Daryl Sarachan, Schenectady, NY (US); Mary Elizabeth Spilker, La Jolla, CA (US)

(73) Assignee: General Electric Company, Niskayuna, NY (US)

( * ) Notice: Subject to any disclaimer, the term of this patent is extended or adjusted under 35 U.S.C. 154(b) by 718 days.

(21) Appl. No.: 12/259,922

(22) Filed: Oct. 28, 2008

(65) Prior Publication Data

US 2010/0106423 A1    Apr. 29, 2010

(51) Int. Cl.
G06G 7/48 (2006.01)
G06G 7/58 (2006.01)
G01N 33/48 (2006.01)
G01N 31/00 (2006.01)

(52) U.S. Cl.
USPC ............. 703/11; 703/12; 702/19; 702/22

(58) Field of Classification Search
None
See application file for complete search history.

(56) References Cited

PUBLICATIONS

Davda et al., (International Immunopharmacology, 2008, 8, 401-413).*
Aubert-Broche et al., (NeuroImage, 2006, 32, 138-145).*
Silva et al. (IEEE Southwest Symposium on Image Analysis and Interpretation, Mar. 24-26, 2008, 61-64).*
Houston et al. (Phys. Med. Biol., 1994, 39, 873-884).*
Seltzer et al. (AJR, 1985, 145, 67-72).*
Mikula et al. (Intern. J. Neuroscience, 2006, 116, 419-429).*
Rippe, B., et al.; "Transport of macromolecules across microvascular walls: the two-pore theory", Physiological Reviews No. 74, Jan. 1994, pp. 163-219.
Zhu, H., et al.; "Potential and limitations of radioimmunodetection and radioimmunotherapy with monoclonal antibodies", Journal of Nucl. Med. 38, (1997) pp. 731-741.
Levitt, D.E.; "PKQuest: a general physiologically based pharmacokinetic model. Introduction and application to propranolol", BMC Clinical Pharmacology 2, Aug. 2002, pp. 1-21.
Leahy, D.E.; "Drug discovery information integration:virtual humans for pharmacokinetics", Biosilico 2, (2004) pp. 78-84.
Parrott, N., et al.; "Application of full physiological models for pharmaceutical drug candidate selection and extrapolation of pharmacokinetics to man", Basic Clinical Pharmacology & Toxicology 96, (2005) pp. 193-199.
Simmons, M., et al.; "A computational positron emission tomography simulation model for imaging beta-amyloid in mice", Mol Imaging Biol 7, (2005) pp. 69-77.
Materi, W., et al.; "Computational systems biology in drug discovery and development: methods and applications", Drug Discovery Today, vol. 12, Nos. 7/8, Apr. 2007, 9 pages.
Mescam, M., et al.; A physiologically based pharmacokinetic model of vascular-extravascular exchanges during liver carcinogenesis: application to MRI contrast agents, Contrast Media & Molecular Imaging 2, (2007), pp. 215-228.
Mescam, M., et al.; Coupling texture analysis and physiological modeling for liver dynamic MRI interpretation, Conf. Proc IEEE Eng. Med. Biol Soc. 1, (2007) pp. 4223-4226.
Barboriak, D.P., et al.; "Comparison of three physiologically-based pharmacokinetic models for the prediction of contrast agent distribution measured by dynamic MR imaging", Journal of Magnetic Resonance Imaging 27, (2008) pp. 1338-1398.

* cited by examiner

*Primary Examiner* — Larry D Riggs, II
(74) *Attorney, Agent, or Firm* — Jenifer Haeckl

(57) ABSTRACT

The quantitative evaluation of biomarker-probe activity is disclosed. In certain embodiments, the biomarker-probe activity may be quantified and analyzed using biodistributions generated using a model. In some embodiments, such biodistributions may be used to generate simulated images from which quantitative thresholds may be derived. In some embodiments, the quantitative thresholds may be used to analyze the biodistributions.

16 Claims, 11 Drawing Sheets

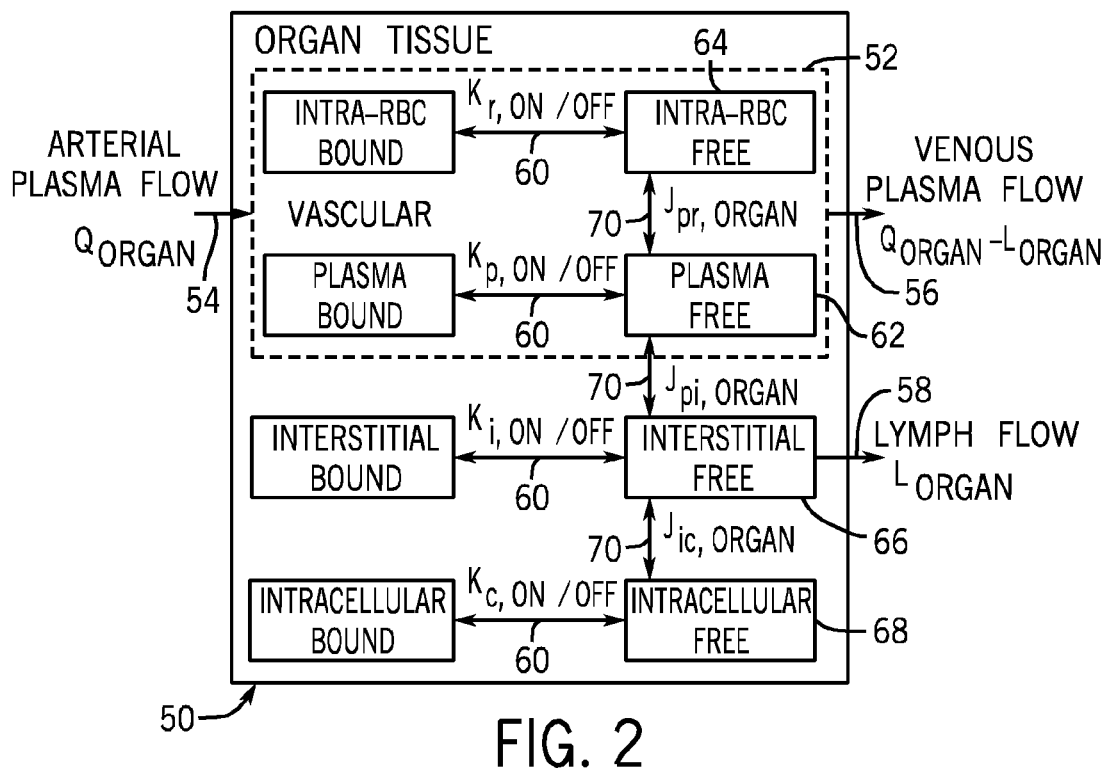
FIG. 2
FIG. 8
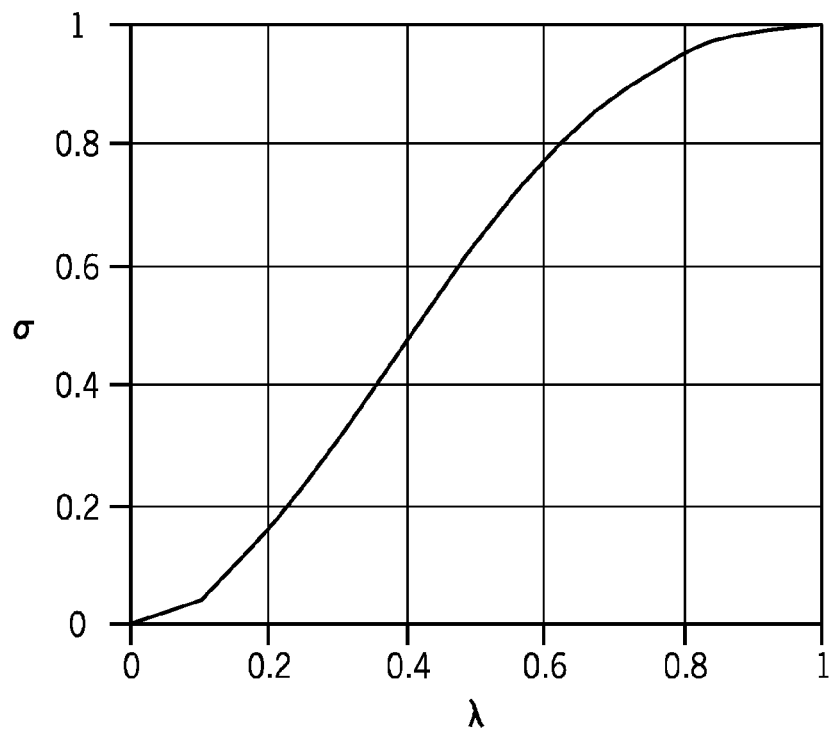

METHOD AND APPARATUS FOR ASSESSING FEASIBILITY OF PROBES AND BIOMARKERS

BACKGROUND OF THE INVENTION

The subject matter disclosed herein relates to medical imaging and, more particularly, to assessing the use of various probes and biomarkers for imaging.

Medical imaging technologies are often used to non-invasively visualize the anatomic and/or metabolic condition of a patient. Traditional imaging technologies rely on nonspecific physical, physiological, or metabolic changes to provide contrast between normal and pathological tissues. In some circumstances, molecular imaging technologies may use specific molecular probes that identify molecular events or attributes that are specific to disease progression (i.e., a biomarker). The probe or a metabolic byprodcut of the probe may then be imaged to provide information about the corresponding biomarker. Therefore, molecular imaging provides a means for non-invasive disease detection, characterization, and therapy monitoring.

However, a suitable probe and/or biomarker may not always be available or known for a given imaging modality (such as positron emission tomography (PET), single positron emission computed tomography (SPECT), magnetic resonance imaging (MRI), and so forth). With regard to the biomarker, to be useful, the concentration of the biomarker should be above the sensitivity limit of the imaging modality and change significantly with the disease progression. With regard to the probe, the probe should have the ability to reach the biomarker, bind strongly to the biomarker, and clear from all surrounding tissues in order to provide good contrast. Further, the kinetics of probe delivery, binding, and clearance may be important factors in view of the particular imaging modality in question. In the absence of a suitable probe and biomarker combination, it may not be possible to successfully utilize an imaging modality to visualize the presence or progression of a biological condition, such as cancer, Alzheimer's disease or atherosclerosis.

BRIEF DESCRIPTION OF THE INVENTION

In one embodiment, a method is provided. In accordance with this method, one or more biodistributions representing biomarker-probe activity are generated using a physiological based pharmacokinetic (PBPK) model. One or more simulated images are generated based on the one or more biodistributions and a digital phantom. The one or more simulated images are quantitatively analyzed to derive one or more numeric classifications of biomarker-probe usefulness for imaging.

In another embodiment, a method is provided. In accordance with this method, one or more numeric thresholds for a biomarker-probe are generated based on simulated images. Each simulated image is generated using a corresponding biodistribution of a plurality of biodistributions. Some or all of the plurality of biodistributions are analyzed using the one or more numeric thresholds.

In a further embodiment, a method is provided. In accordance with this method, an imageability map representing a plurality of predicted biodistributions for a biomarker-probe is reviewed or stored. Each predicted biodistribution is represented by at least one visual classifier corresponding to a quantitative assessment of the respective predicted biodistribution.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein:

FIG. 2 depicts an example of compartments and flow associated with general organ tissue, in accordance with an embodiment of the present disclosure;

FIG. 8 depicts a curve showing the reflection coefficient for a solute molecule as a function of pore radius, in accordance with an embodiment of the present disclosure;

DETAILED DESCRIPTION OF THE INVENTION

The present disclosure describes methods and tools for assessing the feasibility of noninvasive imaging of different biomarkers and probes. In one embodiment, the methods and tools quantify an imaging signal that is expected for a given biomarker, probe, and disease state. Based on the quantified imaging signals, a list of potential biomarkers and probes may be generated and prioritized based on predicted results (such as imagability) in animal models (preclinical) and in humans (clinical). Further, techniques described herein can be used to identify the optimal physical, chemical, and biological properties for various biomarker and probe combinations. Such information may be useful in searching for and evaluating other biomarkers and probes. In addition, the techniques described herein may be used to better understand the mechanism of delivery, binding, biotransformation and clearance of a probe and its impact on imaging.

Figure 1:
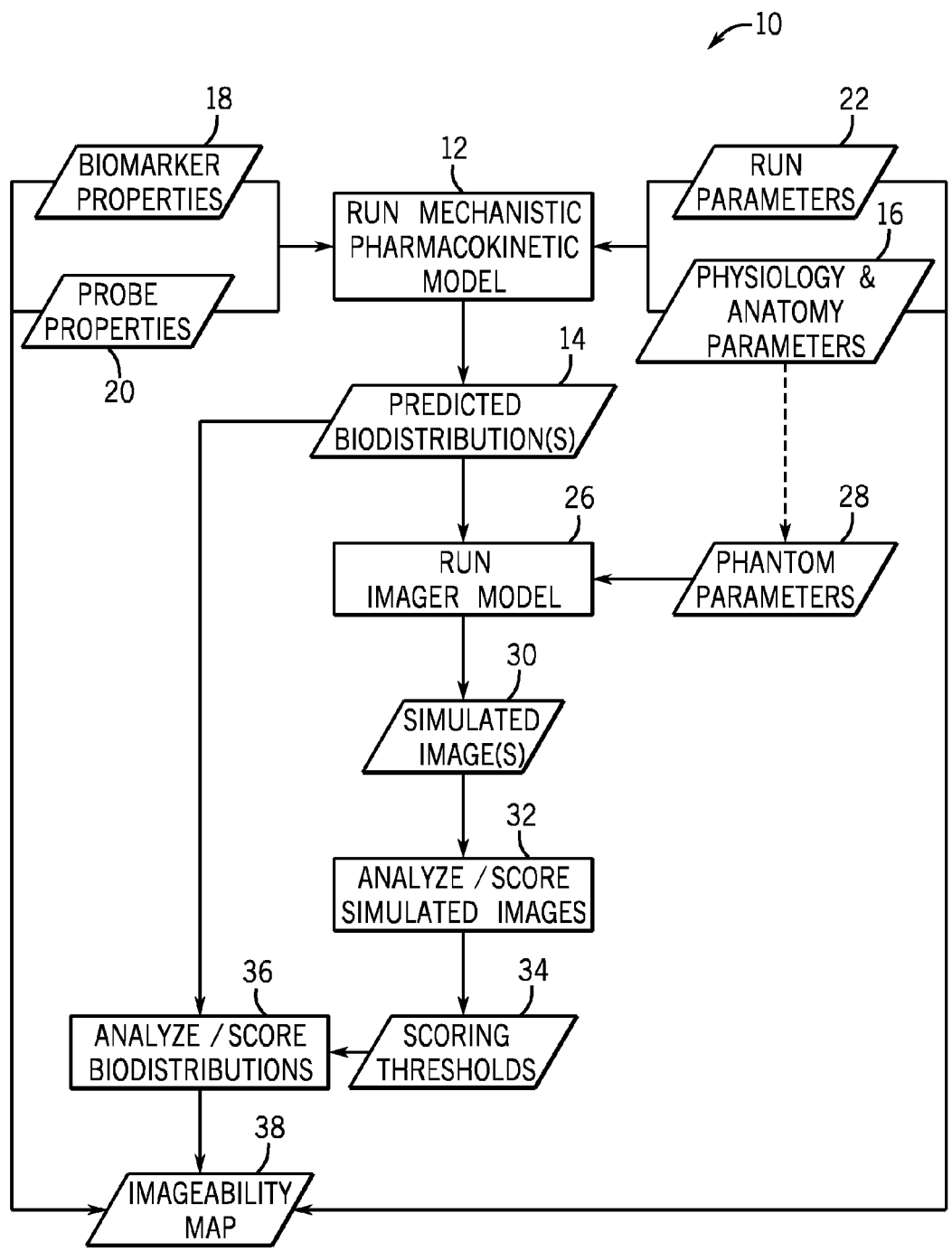
FIG. 1 depicts a flowchart depicting exemplary acts performed in accordance with an embodiment of the present disclosure.

Turning now to FIG. 1, a brief overview of the present technique is provided. As depicted in FIG. 1, a method 10 is illustrated that includes acts that may be executed in performing the present technique. These acts may be embodied as control logic, such as of a computer program or routine, which may be stored and/or executed by a computer. For example, code for implementing the depicted acts may be stored on a mass storage device (such as a solid state memory device, a magnetic storage medium, e.g., a hard drive, and/or an optical storage medium, e.g., an optical disk) of a computer and executed by one or more general or special purpose processors of the computer or workstation. Such an implementation may also involve the use of other components of a computer system typically involved in executing computer programs, displaying or storing results associated with such programs, and/or otherwise communicating inputs and outputs to and from such a computer program. Examples of such other components may include, but are not limited to, ROM, RAM, display circuitry or processors, input devices (e.g., mice, keyboards, keypads, scanners, touchscreens), output devices (e.g., printers, displays), network connections, and so forth.

With regard to the acts depicted in the method 10 of FIG. 1, a physiological based pharmacokinetic (PBPK) computational model is applied (block 12) to generate one or more predicted biodistributions 14 representing the activity of one or more biomarker-probe combinations under various combinations of conditions. In certain embodiments, the PBPK is mechanistic and, therefore, includes kinetic effects, which facilitates the assessment of the molecular imaging feasibility of a probe. Examples of such kinetic effects include probe delivery to the target location, the competition between target and background binding rates and biliary and renal clearance rates. In some embodiments, the PBPK model is implemented using differential equations to represent, at the macro scale, the circulation of fluid through organs and tissues and, at the molecular scale, the biological transport mechanisms and biotransformations within cells and their organelles.

In one embodiment, the PBPK model may be implemented as mechanistic physiological based pharmacokinetic algorithm and/or software codes modeling the distribution, metabolism, and excretion of substances within an organism. For example, the PBPK model may be implemented in Java or other suitable computer programming languages. These algorithms and/or codes may be used to calculate the biodistribution of a probe accounting for delivery, specific and nonspecific binding, biotransformation and clearance of the probe within a human or animal model. For example, the codes may account for the location of a biomarker, biomarker concentration, and changes in biomarker location and/or concentration with the disease progression.

In the depicted embodiment, the inputs for the PBPK model include the physiology & anatomy parameters 16, biomarker properties 18, probe properties 20, and run parameters 22. In one implementation, the physiology and anatomy parameters 16 may be gathered from the literature and may represent parameters for human and/or relevant animal models. Examples of such parameters include body composition, organ/tissue masses, blood flow rates, and so forth. These parameters may be gathered for both a healthy state as well as a disease state.

The biomarker of interest may typically be a protein, carbohydrate, or other molecular structure associated with a target region or a disease state of interest. The biomarker properties 18 provided to the PBPK model may include, among other things, the biomarker concentrations, tissue and sub cellular locations, and how these may change during disease progression.

Typically, molecular imaging probes are composed of an affinity component that interacts, e.g., binds, with the biomarker and a signaling component that is useful for imaging. As used herein, the term probe includes molecular probes, molecular beacons, reporter probes, tracers, smart probes, activatable probes, nanoparticles, and contrast agents. The corresponding probe properties 20 input to the PBPK model may include, among other things, relevant physical and chemical properties for the probe, such as the molecular weight, diffusion coefficient, solubility, pKa, logP/logD, plasma protein binding, substrate for biotransformations and/or active transport associated with the probe.

In addition, run parameters 22 describing the conditions of the simulation may also be provided to the PBPK model. For example, run specific parameters may include the amount of the probe that is injected in the simulation and/or the location of the injection or introduction of the probe to the subject in the simulation. Thus, the run parameters may represent experimental variables that may be varied between runs as opposed to invariable properties of the biomarker or probe being investigated.

The output of the PBPK model may be one or more predicted biodistributions 14 describing the interaction between the probe and biomarker under investigation. The predicted biodistributions 14 may reflect particular biomarker-probe interactions at a particular time, over a particular time interval, and/or for specific physiological locations. For example, a predicted biodistribution 14 may be a time-concentration curve or time-activity curve (TAC), calculated based on the PBPK model and the input parameters, which describes the biodistribution of the probe. In one example, the predicted biodistribution 14 describes the concentration of the probe at any desired time point located in any specific organ tissue down to the vasculature, interstitial, cell cytosol, cell endosomal compartment level.

In the depicted example, an imager model may be run (block 26) to generate one or more simulated images 30. As inputs, the imager model accepts the predicted biodistributions 14 as well as parameters 28 for a phantom. In one embodiment, the imager model may be implemented as one or more imaging modality simulator algorithm and/or software codes that use the predicted biodistributions as inputs to simulate an image using either a human or animal model phantom. The imager model algorithms and/or codes may be based on the underlying physics of the imaging modality being modeled and may account for the probe contrast, change in biomarker, scatter and noise.

Molecular imaging modalities that may be modeled include positron emission tomography (PET), single photon emission computed tomography (SPECT), magnetic resonance imaging (MRI), computed tomography (CT), and ultrasound (US). In one embodiment, a PET simulation maps time-activity curves, i.e., predicted biodistributions 14, for each tissue to their corresponding spatial location in a digital human phantom. For example, a PET imager model may employ scanner characteristics corresponding to the GE DST scanner operating in 2-D mode to generate simulated images 30. In one such embodiment, the simulation software uses this information along with details of the imaging protocol (radiolabel halflife, acquisition start time, duration, and so forth) to generate sinograms with noise characteristic of PET. The sinograms may then be reconstructed using filtered back projection, such as using the ASPIRE program, to generate the simulated images 30.

The phantom parameters 28 employed by the imager model may be geometrically modeled or derived using the physiology and anatomy parameters 16. In one embodiment, the phantom parameters 28 constitute anatomical maps that provide three-dimensional locations in space for each organ of a modeled species. For example, in one implementation a human male (lean) phantom may be used for PET and SPECT image simulations. Thus, phantom parameters may be provided or derived for different species, sexes, body types (lean, average, obese, short, tall, and so forth), or other parameters of interest.

One or more of the simulated images 30 may be quantitatively analyzed and scored (block 32) to determine the extent to which the relevant changes in the disease state can be detected and/or measured. For example, in one embodiment, an analysis may include statistically integrating the intensity function in a region of interest in the simulated image 30 versus the surrounding tissue to assess the effectiveness of a probe in visualizing a biomarker of interest. Based on such quantitative analyses, different biomarker-probe combinations and/or different conditions under which a particular probe and biomarker are being assessed may be ranked or scored in the simulated images 30. Such a scoring scheme based on the simulated images 30 may be used to evaluate the conditions under which a biomarker-probe combination might be acceptable or preferred and/or the conditions under which a biomarker-probe combination might be unacceptable or otherwise not preferred.

In one embodiment, the results of the simulated image scoring process may be used to derive one or more scoring thresholds 34 or set points that may be used to analyze and or score (block 36) the predicted biodistributions 14. For example, in one implementation, a predicted biodistribution 14 may be generated for each combination of a set of factors that define or describe an experiment or clinical diagnostic situation. Of this large set of predicted distributions 14, a smaller subset, such as one, two or three, of the predicted biodistributions 14 may be used as inputs to the image simulation process to generate corresponding simulated images 30. These simulated images may be quantitatively evaluated to derive set points or scoring thresholds 34 that may then be used to evaluate (block 36) the larger set of predicted biodistributions 14 without having to generate a simulated image 30 for each predicted biodistribution 14. In this way, a large set of predicted biodistributions 14 may be quickly, quantitatively and automatically evaluated without subjective human involvement and without having to expend the computational resources necessary to generate simulated images 30 for each predicted biodistribution 14.

In one embodiment, the scoring thresholds 34 derived from the analyses of the simulated images 30 may be simple numeric cutoffs. For example, a threshold may be derived where: $[C_{Tissue}]/[C_{Blood}]<1$ (where $C_{Tissue}$ is the probe concentration in the tissue of interest and $C_{Blood}$ is the probe concentration in the blood) may be deemed not suitable or unsatisfactory due to insufficient image contrast between the tagged and untagged regions while $[C_{Tissue}]/[C_{Blood}]>1$ may be deemed to have suitable or satisfactory contrast. Alternatively, the ratio utilized may be the probe concentration in the tissue of interest relative to the probe concentration in surrounding tissues or some other suitable region that provides context for comparison. In other embodiments, other levels of differentiation may be provided. For example, in one embodiment, a threshold may be derived where: $[C_{Tissue}]/[C_{Blood}]<1$ may be deemed to provide insufficient contrast, $[C_{Tissue}]/[C_{Blood}]>2$ may be deemed to provide sufficient contrast, and $[C_{Tissue}]/[C_{Blood}]>1$ and $<2$ may be indeterminate, i.e., more review or research may be deemed desirable and/or the biomarker-probe combination may provide sufficient contrast to be used in certain scenarios.

In addition to the thresholds 34 derived from the simulated images 30, the scoring of the biodistributions may take into account the loss in signal due to the scattering and noise in the imaging modality of interest, such as PET, SPECT, MRI, CT, or US. In addition, the biodistribution scoring may account for the changes in the probe concentration that are required to measure changes in the disease state. Further, the biodistribution scoring process, utilizing the scoring thresholds 34 derived from analyses of some or all of the simulated images 30, may account for the differences in probe concentration at the biomarker location versus the neighboring background tissues, i.e., the staining or tagging efficacy of the probe under the stipulated circumstances, as explained above.

The results of the analyses of the predicted biodistributions 14 may be summarized and/or visually provided in a report where the efficacy of a probe and biomarker combination can be evaluated for each of the different combinations of factors used to generate the biodistributions 14. In one embodiment, this summary may be provided as an imageability map 38. Such an imageability map 38 may present the probability of success of imaging for all property combinations of the biomarker and probe under review. For example, with the scoring of the biodistributions 14 determined, the set of biomarker-probe properties required for adequate imaging can be determined for various biomarker locations (e.g. interstitial, cell membrane, cytosol, cell vesicles) and various probe properties (molecular weight, pKas, logP/logD).

With the foregoing general overview in mind, implementations of aspects of the present technique will be discussed in greater detail. With regard to the PBPK model, in one implementation, the tissue of each organ of the body was modeled by dividing it up into a number of compartments that define a spatial location and the state of the probe, e.g., a tracer agent. In such an implementation, the concentration of the probe within each compartment may be assumed to be uniform. The spatial locations may include the organ's vascular, interstitial, and intracellular spaces. The vascular space may be further subdivided into the plasma and the intra red blood cell (RBC) spaces.

The state of the probe may be defined as either free or bound. If the probe is in the bound state, then it may be assumed to be bound to some other molecular element located at the same spatial location. The plasma protein albumin is an example of a molecular element that the probe could bind to in the vascular plasma space. The state of the probe may also be used to define other forms or conformations of the probe. For example, the original probe may undergo a bio-transformation into another form that exhibits a different degree of hydrophobicity. In such an example, the different forms and/or conformations of the probe may constitute different states of the probe for model purposes.

Turning to FIG. 2, an example of different compartments and flows for generalized organ tissue 50 is depicted. In this example, the arrows depict the flow of the probe between the various compartments that represent changes in the probe's spatial location or binding state. The probe can flow convectively into the vascular compartments 52 of the organ tissue 50 via the plasma flow ($Q_{organ}$) 54. The probe can also convectively flow out of the organ tissue 50 by either the venous plasma flow 56 or by the lymph flow ($L_{organ}$) 58.

In one implementation, to maintain the mass balance, the "in" flow rate must equal the "out" flow rate of the organ tissue 50, which makes the venous plasma flow 56 equal to ($Q_{organ}-L_{organ}$). The probe can either associate or disassociate with molecular elements to become either bound or free as described by the flow rates 60 ($K_{on}$) and ($K_{off}$) respectively. These flow rates 60 represent a change in the binding of the probe and not a change in its spatial location. These flow rates 60 may be defined at the vascular plasma (p), intra RBC (r), interstitial (i), and intracellular (c) spatial locations of the organ tissue 50. The probe, when it is in its free state, can be transported between the vascular plasma 62, intra RBC 64, interstitial 66, and intracellular compartments 68 as depicted by the represented flow paths 70. The rate of transport between these compartments may be described by the flow rates ($J_{pr,organ}$), ($J_{pi,organ}$) and ($J_{ic,organ}$). These flow rate terms are the summation of multiple transport mechanisms that move the probe across cell membranes and/or through aqueous pores and clefts between cells. Modes of transport modeled may include, but are not limited to, passive diffusion, convective flow, vesicular transport and/or active transport mechanisms. All of these mechanisms and paths may be aggregated into a single flow term represented by the terms ($J_{pr,organ}$), ($J_{pi,organ}$) and ($J_{ic,organ}$).

Figure 3:
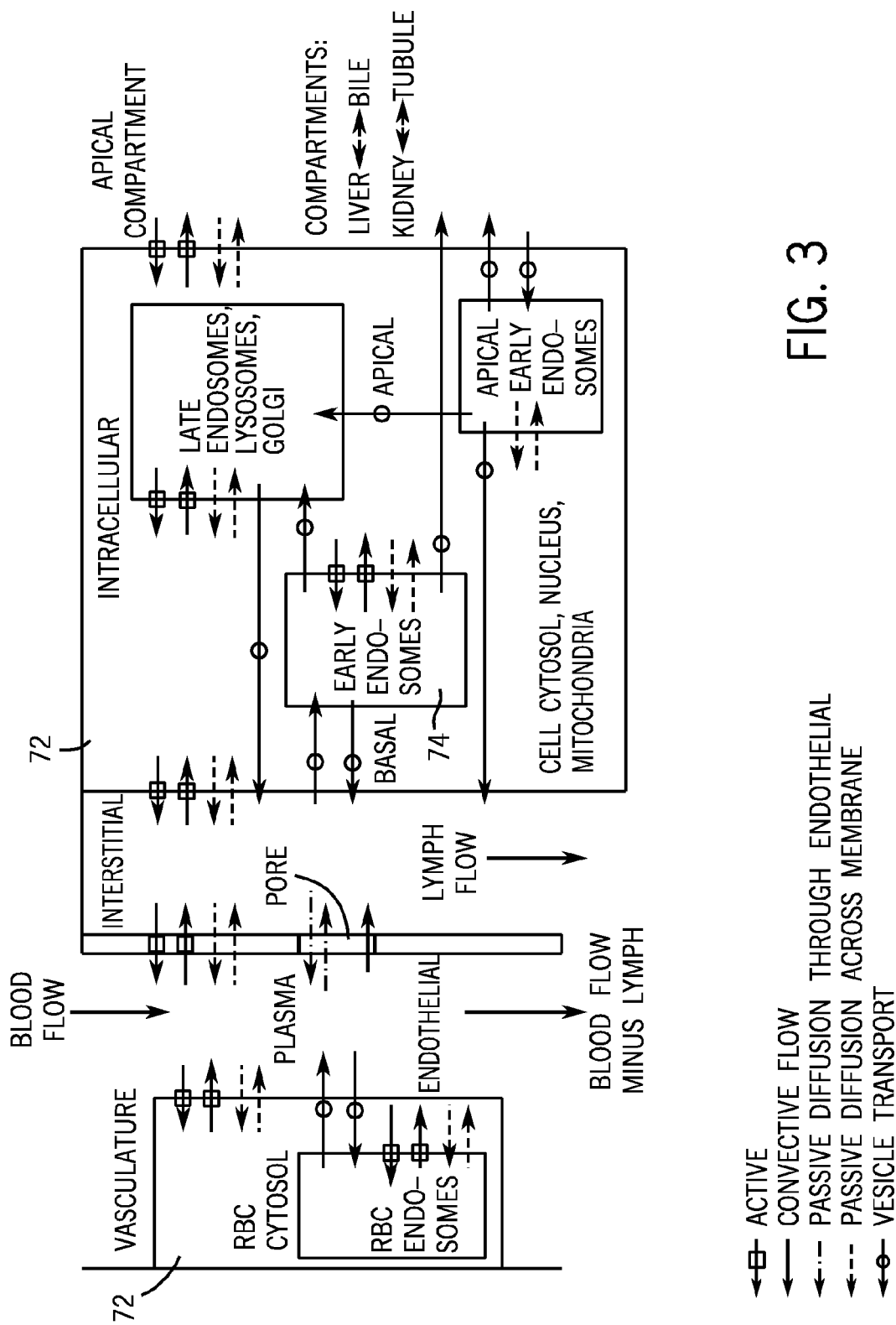
FIG. 3 depicts cellular compartments and flows, in accordance with an embodiment of the present disclosure.

While FIG. 2, describes the various flows that may be modeled between the various compartments of a tissue, in certain embodiments the PBPK model may also model the organism of interest down to the cellular or subcellular level. For example, referring now to FIG. 3, the subcellular level may be modeled to include the cytosol 72, early endosome 74, Golgi, and other organelles. Furthermore, some cells in the model may be polarized, having both a basal and apical cell plasma membrane. Examples include the epithelial cells lining the proximal tubules of the kidney tissue and hepatocytes of the liver tissue.

Figure 4:
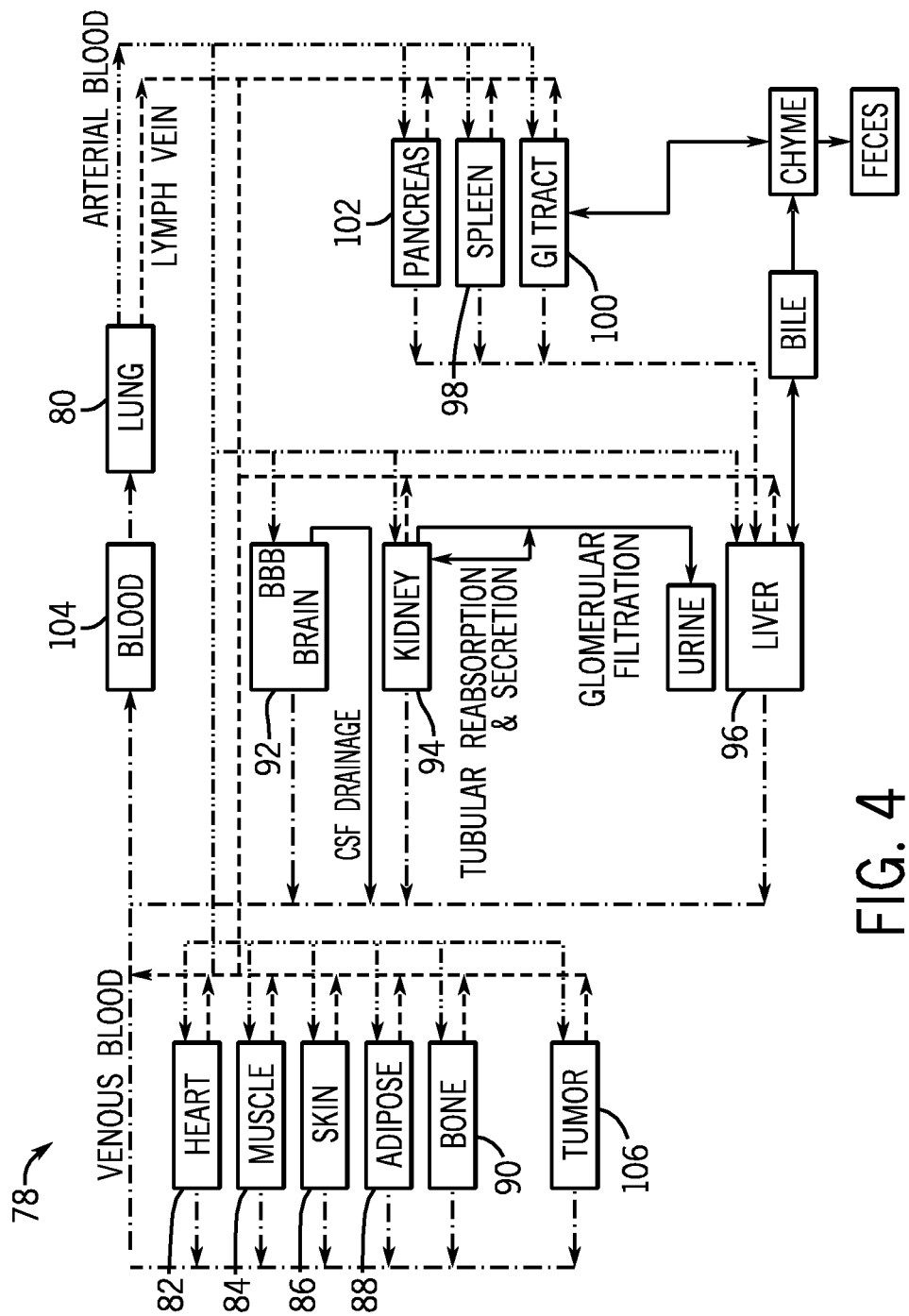
FIG. 4 depicts the organs and tissues included in a general physiological based PBPK, in accordance with an embodiment of the present disclosure.
Figure 5:
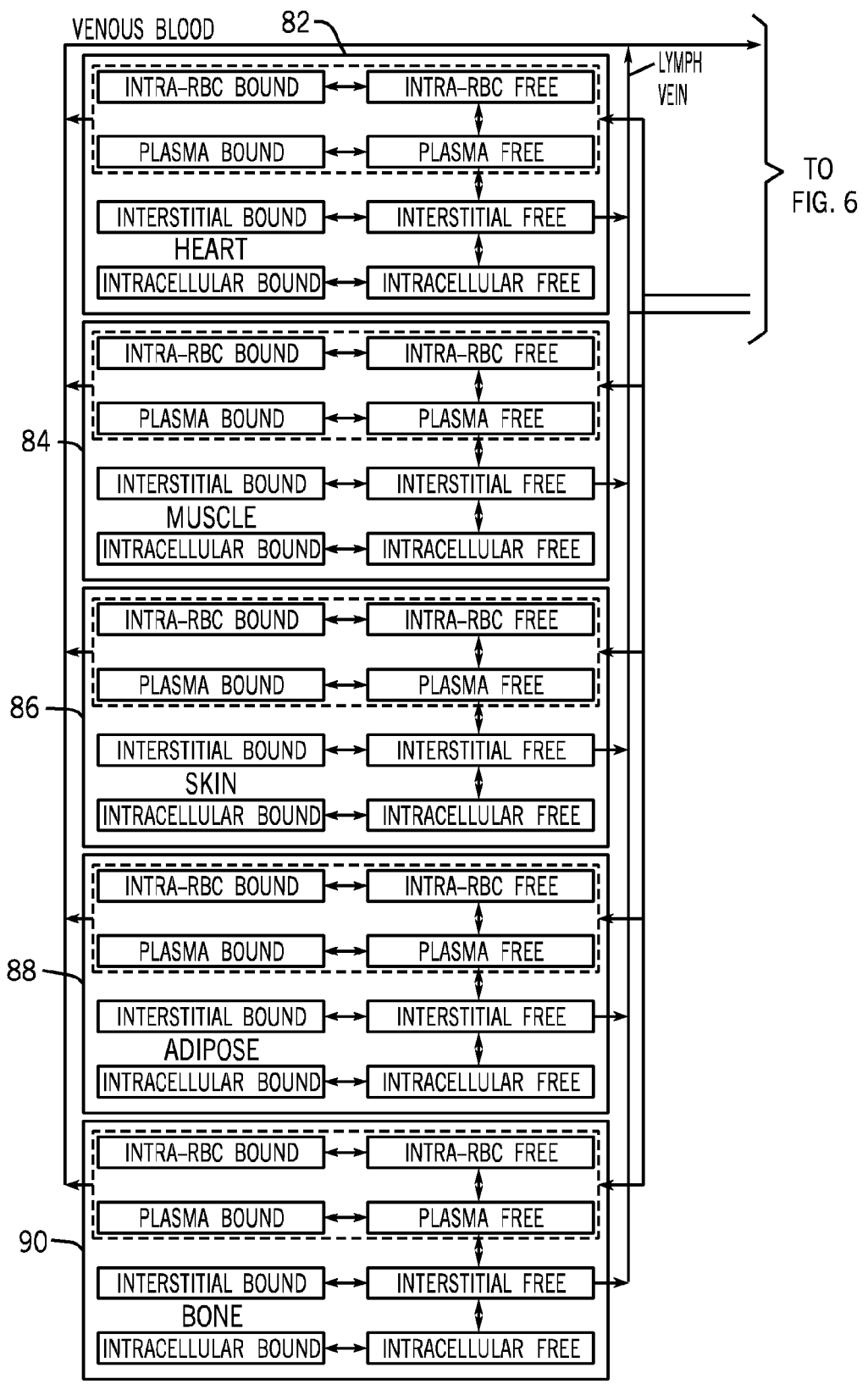
FIGS. 5-6, in combination, depict the organs and tissues included in a general physiological based PBPK along with intraorgan compartments, in accordance with an embodiment of the present disclosure.
Figure 6:
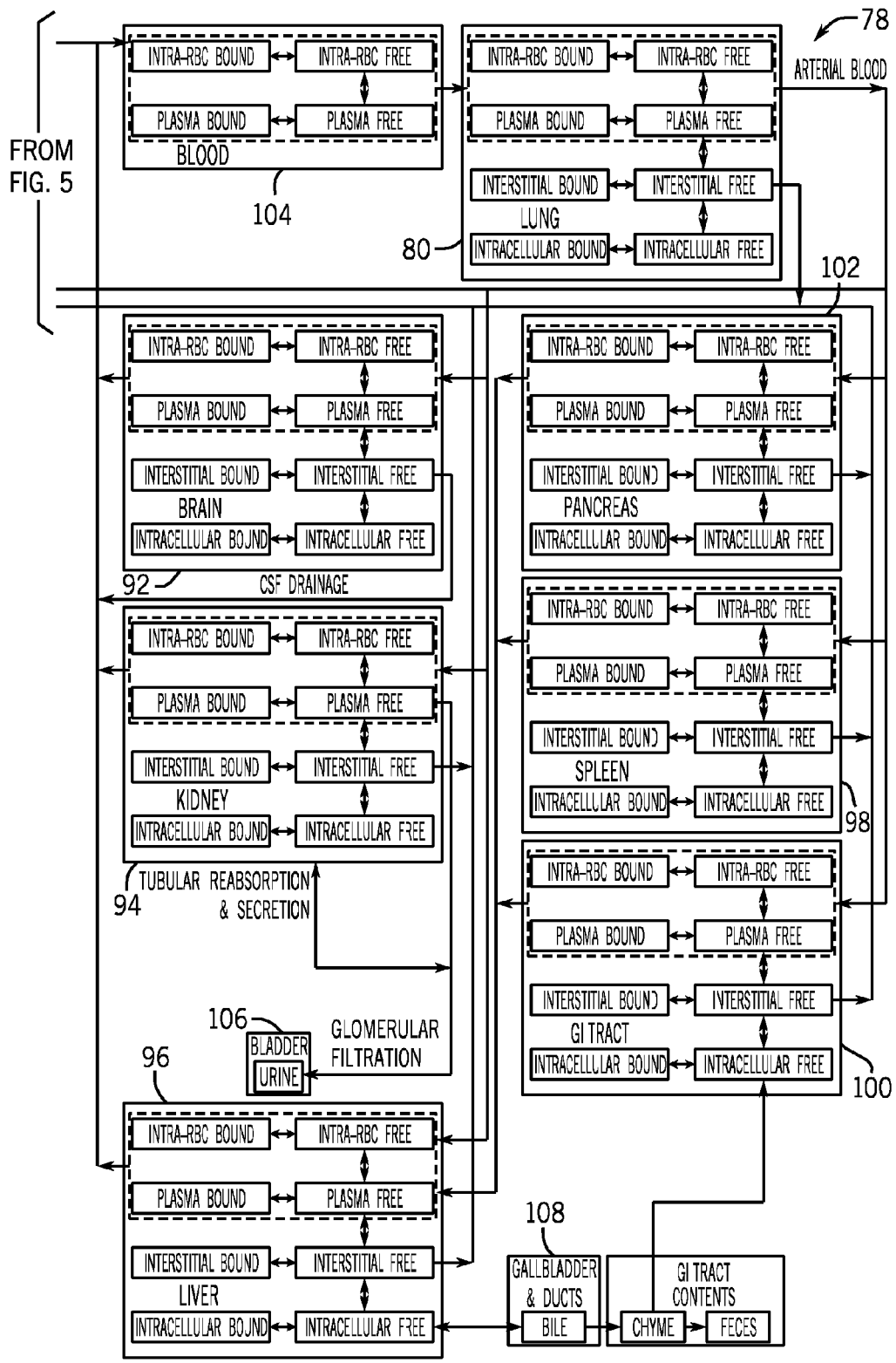

Turning now to FIG. 4 and FIGS. 5-6, a high level and detailed view of organs and tissues accounted for in one embodiment of a general PBPK model 78 are respectively depicted. FIG. 4 depicts the organs and that may be represented in a general PBPK model while FIGS. 5-6, in combination, depict the organs and tissues along with the intraorgan compartments and flows as described above with respect to FIG. 2. In one implementation, the organs, tissues, compartments, and flows depicted in FIGS. 5-6 represent the possible flow paths of one example of a PBPK model 78. In this example, the included features, here the lung 80, heart 82, muscle 84, skin 86, adipose (fat) 88, bone 90, brain 92, kidney 94, liver 96, spleen 98, gastrointestinal (GI) tract 100, pancreas 102, and blood 104 have the same compartments as described in FIG. 2.

In FIGS. 4 and 5-6, the arterial flow represents the oxygenated blood leaving the lungs 80 and the venous flow represents the partially deoxygenated blood returning to the lungs 80. In this depiction, the blood plasma and intra-RBC free and bound compartments represents the total volume of blood not already accounted for by the vascular compartments within each organ tissue. The location of this blood is in the major arteries and veins of the body and may be considered separate from any of the specific organ tissues defined in the depicted PBPK model 78.

Brain tissue does not have true lymphatics. However, the cerebrospinal fluid (CSF) flows through the brain tissues and passes out through the perivascular spaces into the subarachnoid spaces. Here, the CSF can be absorbed through the arachnoidal villi into the larger cerebral veins. The flow is one way and is dependent upon the CSF pressure being greater than the venous pressure. This brain flow path is shown in FIGS. 4 and 5-6 by a line labeled CSF drainage.

In the depicted PBPK model 78 the kidney 94 includes the flow paths for the glomerular filtration, tubular reabsorption, and secretion. In the depicted implementation, only the probe within the kidney's plasma free compartment is filtered. The probe within the plasma bound compartment is considered to be attached to large plasma proteins like albumin. Albumin has a very low glomerular filterability coefficient (0.005 albumin vs. 1 for water) due to its size and net negative charge. The urine compartment represents the urine that is physically located in the bladder 106 and any urine excreted by the body.

In the depicted PBPK model 78 the liver 96 includes a number of additional flow paths from the general organ. First the incoming vascular flow to the liver 96 comes from both the hepatic artery and the portal vein. The portal vein receives the blood from the venous outflow of the gastrointestinal (GI) tract 100 and spleen 98. Within the liver organ 96, the probe can also flow across the canalicular membrane of the hepatocyte and into the bile canaliculi. The convective flow of the bile travels down the hepatic duct and the common bile duct and can be diverted through the cystic duct into the gallbladder 108. This is shown in the depicted PBPK model 78 as a flow path from the liver's intracellular free compartment into the bile compartment. The bile compartment includes the contents of all of the gallbladder 108 and all of the bile ducts. The probe in the bile can then flow through the common bile duct to be secreted into the duodenum of the GI tract. This is shown as the arrow from the bile compartment into the chyme compartment. Probe within the chyme (i.e. contents of the digestive tube) can be reabsorbed by the small intestines and flow into the GI tract 100 interstitial free compartment. The other path is for the probe to remain in the chyme that passes through the ileocecal valve into the colon to be concentrated down into feces. This is represented in the depicted PBPK model 78 as the flow from the chyme compartment to the feces compartment. The feces compartment represents the contents of the storage portion of the large intestines and any feces excreted by the body.

In one embodiment, differential equations may be used to describe the changes in concentration of a probe within the eight compartments represented for each organ in FIGS. 2 and 5-6. An example set of such equations, labeled equations 1-8, include the following:

plasma free compartment:

$$\left(\frac{dC_{pf,organ}}{dt}\right) = \frac{1}{V_{p,organ}}\{Q_{organ}C_{pf,lung} - (Q_{organ} - L_{organ})C_{pf,organ} - J_{pr,organ} - J_{pi,organ}\} - K_{p,on}C_{pf,organ} + K_{p,off}C_{pb,organ} \quad (1)$$

plasma bound compartment:

$$\left(\frac{dC_{pb,organ}}{dt}\right) = \frac{1}{V_{p,organ}}\{Q_{organ}C_{pb,lung} - (Q_{organ} - L_{organ})C_{pb,organ}\} + K_{p,on}C_{pf,organ} - K_{p,off}C_{pb,organ} \quad (2)$$

intra-RBC free compartment:

$$\left(\frac{dC_{rf,organ}}{dt}\right) = \quad (3)$$

$$\frac{1}{V_{r,organ}}\{Q_{organ}C_{rf,lung} - (Q_{organ} - L_{organ})C_{rf,organ} - J_{pr,organ}\} - K_{r,on}C_{rf,organ} + K_{r,off}C_{rb,organ}$$

intra-RBC bound compartment:

$$\left(\frac{dC_{rb,organ}}{dt}\right) = \frac{1}{V_{r,organ}}\{Q_{organ}C_{rb,lung} - (Q_{organ} - L_{organ})C_{rb,organ}\} + K_{r,on}C_{rf,organ} - K_{r,off}C_{rb,organ} \quad (4)$$

interstitial free compartment:

$$\left(\frac{dC_{if,organ}}{dt}\right) = \frac{1}{V_{i,organ}}\{J_{pi,organ} - J_{ic,organ} - L_{organ}C_{if,organ}\} - K_{i,on}C_{if,organ} + K_{i,off}C_{ib,organ} \quad (5)$$

interstitial bound compartment:

$$\left(\frac{dC_{ib,organ}}{dt}\right) = K_{i,on}C_{if,organ} - K_{i,off}C_{ib,organ} \quad (6)$$

intracellular free compartment:

$$\left(\frac{dC_{cf,organ}}{dt}\right) = \frac{1}{V_{c,organ}}\{J_{ic,organ}\} - K_{c,on}C_{cf,organ} + K_{c,off}C_{cb,organ} \quad (7)$$

intracellular bound compartment:

$$\left(\frac{dC_{cb,organ}}{dt}\right) = K_{c,on}C_{cf,organ} - K_{c,off}C_{cb,organ} \quad (8)$$

where C stands for concentration of the probe within the organ compartment defined by the subscript which is either plasma free (pf), plasma bound (pb), intra-RBC free (rf), intra-RBC bound (rb), interstitial free (if), interstitial bound (ib), intracellular free (cf), or intracellular bound (cb); V stands for the volume of the organ compartment defined by the subscript which is either plasma (p), intra-RBC (r), interstitial (i), or intracellular (c); Q stands for plasma flow and L stands for the lymph flow with the subscripts defining the organ; J stands for the physical transport of the probe between the plasma and the intra-RBC (pr) spaces; between the plasma and interstitial (pi) spaces; and between the interstitial and intercellular (ic) spaces of the organ; and K stands for the association (on) and disassociation (off) rates for the probe to change between the free and bound states within the four main spaces of the organ. All of the organ tissues use the ordinary differential equations presented in equations 1-8 with some exceptions, discussed below, for the lung, kidney, liver, and GI tract. In certain embodiments, a tumor 106, as represented in the PBPK model of FIGS. 4 and 5-6, may be represented as organ tissue or structure having the same compartments and flow paths as the described organs and beign represented by the same equations, i.e., equations 1-8 in the described implementation.

In addition, differential equations may be used to describe the change in concentration of a probe within the blood, such as where the blood is represented by the blood compartments depicted in FIGS. 2 and 5-6. An example set of such equations, labeled equations 9-12, include the following:

plasma free compartment:

$$\left(\frac{dC_{pf,blood}}{dt}\right) = \quad (9)$$

$$\frac{1}{V_{p,blood}}\{(Q_{heart} - L_{heart})C_{pf,heart} + (Q_{muscle} - L_{muscle})C_{pf,muscle} +$$

$$(Q_{skin} - L_{skin})C_{pf,skin} + (Q_{adipose} - L_{adipose})C_{pf,adipose} +$$

$$(Q_{bone} - L_{bone})C_{pf,bone} + (Q_{brain} - L_{brain}^{csf})C_{pf,brain} +$$

$$(Q_{kidney} - L_{kidney})C_{pf,kidney} + (Q_{liver} - L_{liver})C_{pf,liver} -$$

$$Q_{lung}C_{pf,plasma} + L_{lung}C_{if,lung} + L_{heart}C_{if,heart} +$$

$$L_{muscle}C_{if,muscle} + L_{skin}C_{if,skin} + L_{adipose}C_{if,adipose} +$$

$$L_{bone}C_{if,bone} + L_{brain}^{csf}C_{if,brain} + L_{kidney}C_{if,kidney} +$$

-continued $$L_{liver}C_{if,liver} + L_{spleen}C_{if,spleen} + L_{gi}C_{if,gi} - J_{pr,organ}\} -$$

$$K_{p,on}C_{pf,plasma} + K_{p,off}C_{pb,plasma}$$

plasma bound compartment:

$$\left(\frac{dC_{pb,blood}}{dt}\right) = \quad (10)$$

$$\frac{1}{V_{p,blood}}\{(Q_{heart} - L_{heart})C_{pb,heart} + (Q_{muscle} - L_{muscle})C_{pb,muscle} +$$

$$(Q_{skin} - L_{skin})C_{pb,skin} + (Q_{adipose} - L_{adipose})C_{pb,adipose} +$$

$$(Q_{bone} - L_{bone})C_{pb,bone} + (Q_{brain} - L_{brain}^{csf})C_{pb,brain} +$$

$$(Q_{kidney} - L_{kidney})C_{pb,kidney} + (Q_{liver} - L_{liver})C_{pb,liver} -$$

$$Q_{lung}C_{pb,plasma}\} + K_{p,on}C_{pf,plasma} - K_{p,off}C_{pb,plasma}$$

intra RBC free compartment:

$$\left(\frac{dC_{rf,blood}}{dt}\right) = \quad (11)$$

$$\frac{1}{V_{r,blood}}\{(Q_{heart} - L_{heart})C_{rf,heart} + (Q_{muscle} - L_{muscle})C_{rf,muscle} +$$

$$(Q_{skin} - L_{skin})C_{rf,skin} + (Q_{adipose} - L_{adipose})C_{rf,adipose} +$$

$$(Q_{bone} - L_{bone})C_{rf,bone} + (Q_{brain} - L_{brain}^{csf})C_{rf,brain} +$$

$$(Q_{kidney} - L_{kidney})C_{rf,kidney} + (Q_{liver} - L_{liver})C_{rf,liver} -$$

$$Q_{lung}C_{rf,plasma} + J_{pr,organ}\} - K_{r,on}C_{rf,plasma} + K_{r,off}C_{rb,plasma}$$

intra RBC bound compartment:

$$\left(\frac{dC_{rb,blood}}{dt}\right) = \quad (12)$$

$$\frac{1}{V_{r,blood}}\{(Q_{heart} - L_{heart})C_{rb,heart} + (Q_{muscle} - L_{muscle})C_{rb,muscle} +$$

$$(Q_{skin} - L_{skin})C_{rb,skin} + (Q_{adipose} - L_{adipose})C_{rb,adipose} +$$

$$(Q_{bone} - L_{bone})C_{rb,bone} + (Q_{brain} - L_{brain}^{csf})C_{rb,brain} +$$

$$(Q_{kidney} - L_{kidney})C_{rb,kidney} + (Q_{liver} - L_{liver})C_{rb,liver} -$$

$$Q_{lung}C_{rb,plasma}\} + K_{r,on}C_{rf,plasma} - K_{r,off}C_{rb,plasma}$$

Differential equations may also be used to preserve the mass balance. For example, two flow constraint equations may be employed to maintain the mass balance of the modeled system. An example set of such equations, labeled equations 13-14, include the following:

volumetric flow rate constraint 1:

$$Q_{blood} = Q_{lung} = L_{lung} + Q_{heart} + Q_{muscle} + Q_{skin} + Q_{adipose} + Q_{bone} + Q_{brain} + Q_{kidney} + Q_{hepatic} + Q_{spleen} + Q_{gi} \quad (13)$$

volumetric flow rate constraint 2:

$$Q_{liver} = Q_{hepatic} + Q_{spleen} - L_{speen} + Q_{gi} - L_{gi}. \quad (14)$$

As illustrated in FIGS. 5-6, the plasma flow to the lungs come from the blood compartments. An example of a set of differential equations modeling plasma flow to the lungs, labeled equations 15-18, include the following:

lung plasma free compartment:

$$\left(\frac{dC_{pf,organ}}{dt}\right) = \tag{15}$$
$$\frac{1}{V_{p,organ}}\{Q_{organ}C_{pf,blood} - (Q_{organ} - L_{organ})C_{pf,organ} - J_{pr,organ} - J_{pi,organ}\} - K_{p,on}C_{pf,organ} + K_{p,off}C_{pb,organ}$$

lung plasma bound compartment:

$$\left(\frac{dC_{pb,organ}}{dt}\right) = \tag{16}$$
$$\frac{1}{V_{p,organ}}\{Q_{organ}C_{pb,blood} - (Q_{organ} - L_{organ})C_{pb,organ}\} + K_{p,on}C_{pf,organ} - K_{p,off}C_{pb,organ}$$

lung intra-RBC free compartment:

$$\left(\frac{dC_{rf,organ}}{dt}\right) = \tag{17}$$
$$\frac{1}{V_{r,organ}}\{Q_{organ}C_{rf,blood} - (Q_{organ} - L_{organ})C_{rf,organ} + J_{pr,organ}\} - K_{r,on}C_{rf,organ} + K_{r,off}C_{rb,organ}$$

lung intra-RBC bound compartment:

$$\left(\frac{dC_{rb,organ}}{dt}\right) = \frac{1}{V_{r,organ}}\{Q_{organ}C_{rb,blood} - (Q_{organ} - L_{organ})C_{rb,organ}\} + K_{r,on}C_{rf,organ} - K_{r,off}C_{rb,organ}. \tag{18}$$

As illustrated in FIGS. 5-6, the kidneys have two exceptions to account for including the glomerular filtration, tubular reabsorption and secretion. An example of a set of differential equations modeling the kidneys, labeled equations 19-20, include the following:

kidney plasma free compartment:

$$\left(\frac{dC_{pf,kidney}}{dt}\right) = \tag{19}$$
$$\frac{1}{V_{p,kidney}}\{Q_{kidney}C_{pf,lung} - (Q_{kidney} - L_{kidney})C_{pf,organ} - J_{pr,kidney} - J_{pi,kidney} - J_{filtration,kidney}\} - K_{p,on}C_{pf,kidney} + K_{p,off}C_{pb,kidney}$$

kidney interstitial free compartment:

$$\left(\frac{dC_{if,kidney}}{dt}\right) = \tag{20}$$
$$\frac{1}{V_{i,kidney}}\{J_{pi,kidney} - J_{ic,organ} - L_{kidney}C_{if,kidney} + J_{reabsorption,kidney}\} - K_{i,on}C_{if,kidney} + K_{i,off}C_{ib,kidney}.$$

As illustrated in FIGS. 5-6, the liver has several exceptions to handle including the hepatic artery and the portal vein plasma inflow and the bile secretion flow. An example of a set of differential equations modeling the liver, labeled equations 21-25, include the following:

liver plasma free compartment:

$$\left(\frac{dC_{pf,liver}}{dt}\right) = \tag{21}$$
$$\frac{1}{V_{p,liver}}\{(Q_{gi} - L_{gi})C_{pf,gi} + (Q_{spleen} - L_{spleen})C_{pf,spleen} + Q_{hepatic}C_{pf,lung} - (Q_{liver} - L_{liver})C_{pf,liver} - J_{pr,liver} - J_{pi,liver}\} - K_{p,on}C_{pf,liver} + K_{p,off}C_{pb,liver}$$

liver plasma bound compartment:

$$\left(\frac{dC_{pb,liver}}{dt}\right) = \frac{1}{V_{p,liver}}\{(Q_{spleen} - L_{spleen})C_{pd,spleen} + (Q_{gi} - L_{gi})C_{pd,gi} + Q_{hepatic}C_{pb,lung} - (Q_{liver} - L_{liver})C_{pb,liver}\} + K_{p,on}C_{pf,liver} - K_{p,off}C_{pb,liver} \tag{22}$$

liver intra-RBC free compartment:

$$\left(\frac{dC_{rf,liver}}{dt}\right) = \frac{1}{V_{r,liver}}\{(Q_{gi} - L_{gi})C_{rf,gi} + (Q_{spleen} - L_{spleen})C_{rf,spleeni} + Q_{hepatic}C_{rf,lung} - (Q_{liver} - L_{liver})C_{rf,liver} + J_{pr,liver}\} - K_{r,on}C_{rf,liver} + K_{r,off}C_{rb,liver} \tag{23}$$

liver intra-RBC bound compartment:

$$\left(\frac{dC_{rb,liver}}{dt}\right) = \frac{1}{V_{r,liver}} \tag{24}$$
$$\{(Q_{spleen} - L_{spleen})C_{rb,spleen} + (Q_{gi} - L_{gi})C_{rb,gi} + Q_{hepatic}C_{rb,lung} - (Q_{liver} - L_{liver})C_{rb,liver}\} + K_{r,on}C_{rf,liver} - K_{r,off}C_{rb,liver}$$

liver intracellular free compartment:

$$\left(\frac{dC_{cf,liver}}{dt}\right) = \tag{25}$$
$$\frac{1}{V_{c,liver}}\{J_{ic,liver} - J_{cbile,liver}\} - K_{c,on}C_{cf,liver} + K_{c,off}C_{cb,liver}.$$

In the depicted implementation of FIGS. 5-6, the GI tract has one exception to handle which is the chyme absorption flow path. An example of a differential equation modeling the GI tract, labeled equation 26, is the following:

GI tract interstitial free compartment:

$$\left(\frac{dC_{if,gi}}{dt}\right) = \frac{1}{V_{i,gi}}\{J_{vi,gi} - J_{ic,gi} - L_{gi}C_{if,gi} + J_{absorption,gi}\} - K_{i,on}C_{if,gi} + K_{i,off}C_{ib,gi}. \tag{26}$$

With regard to the remainder of the PBPK model described by FIGS. 5-6, the urine, bile, chyme, and feces compartments may also be described by respective differential equations. Examples of such differential equations, labeled equations 27-30, are as follows:

urine compartment:

$$\left(\frac{dC_{urine}}{dt}\right) = \frac{1}{V_{urine}}\{J_{filtration,kidney} - J_{reabsorption,kidney}\} \quad (27)$$

bile compartment:

$$\left(\frac{dC_{bile}}{dt}\right) = \frac{1}{V_{bile}}\{J_{bile,liver} - J_{bile,chyme}\} \quad (28)$$

chyme compartment:

$$\left(\frac{dC_{chyme}}{dt}\right) = \frac{1}{V_{chyme}}\{J_{bile,chyme} - J_{absorption,gi} - J_{chyme,feces}\} \quad (29)$$

feces compartment:

$$\left(\frac{dC_{feces}}{dt}\right) = \frac{1}{V_{feces}}\{J_{chyme,feces}\}. \quad (30)$$

The differential equations presented in equations 1-30 for the general PBPK model depicted in FIGS. 5-6 have input parameters that include the plasma flow rates, Q, the lymph flow rates, L, the volumes of the compartments, V, and the probe flow rates between the compartments for both spatial location, J, and binding state, K. With these five sets of input parameters, an ordinary differential equation solver may be used to calculate the concentration of probe, C, in the various compartments at any given time point.

With the foregoing in mind, an example of a methodology that may be used to calculate compartment flow rates for both transport between spatial locations and changes in binding state is discussed. Passive diffusion is one mechanism for the transport of small molecules between the vascular and interstitial compartments. The passive diffusion process allows the molecule to pass across the cell membranes of the capillary endothelium. However, this mechanism is typically limited to lipid soluble molecules. Another transport mechanism is the diffusion and/or convective transport through the intercellular pores in the capillary membrane. The pores are created by the intercellular clefts between the endothelial cells. This mechanism allows the transport of molecules that are lipid insoluble as long as their size is smaller than the pore size.

In one implementation of a PBPK model, the two-pore theory was used to model the passive transport of molecules across the microvascular walls. Passive diffusion is one mechanism for the transport of small molecules between the vascular and interstitial compartments. The passive diffusion process allows a molecule to cross the cell membranes of the capillary endothelium. However, this mechanism may apply most readily to lipid soluble molecules that do not have charges. Other transport mechanisms include the diffusion and/or convective transport through pores in the capillary membrane. The pores represent the intercellular clefts between the endothelial cells and endothelial fenestrations. These pores allow the transport of molecules that are lipid insoluble as long as their size is smaller than the pore size, as discussed below.

The two-pore theory does not account for other possible transport mechanisms including transcytosis and receptor-mediated transcytosis. However, the bulk transport of plasma proteins from blood to the interstitial space is understood to follow first-order kinetics and not Michaelis-Menten kinetics as expected for the transcytosis mechanisms. So in one implementation of the PBPK model, it may be assumed that there is no transcytosis or receptor-mediated transcytosis of the probe across the microvascular walls. Other implementations of the PBPK model could model the transcytosis or receptor-mediated transcytosis of the probe across the microvascular walls.

Figure 7:
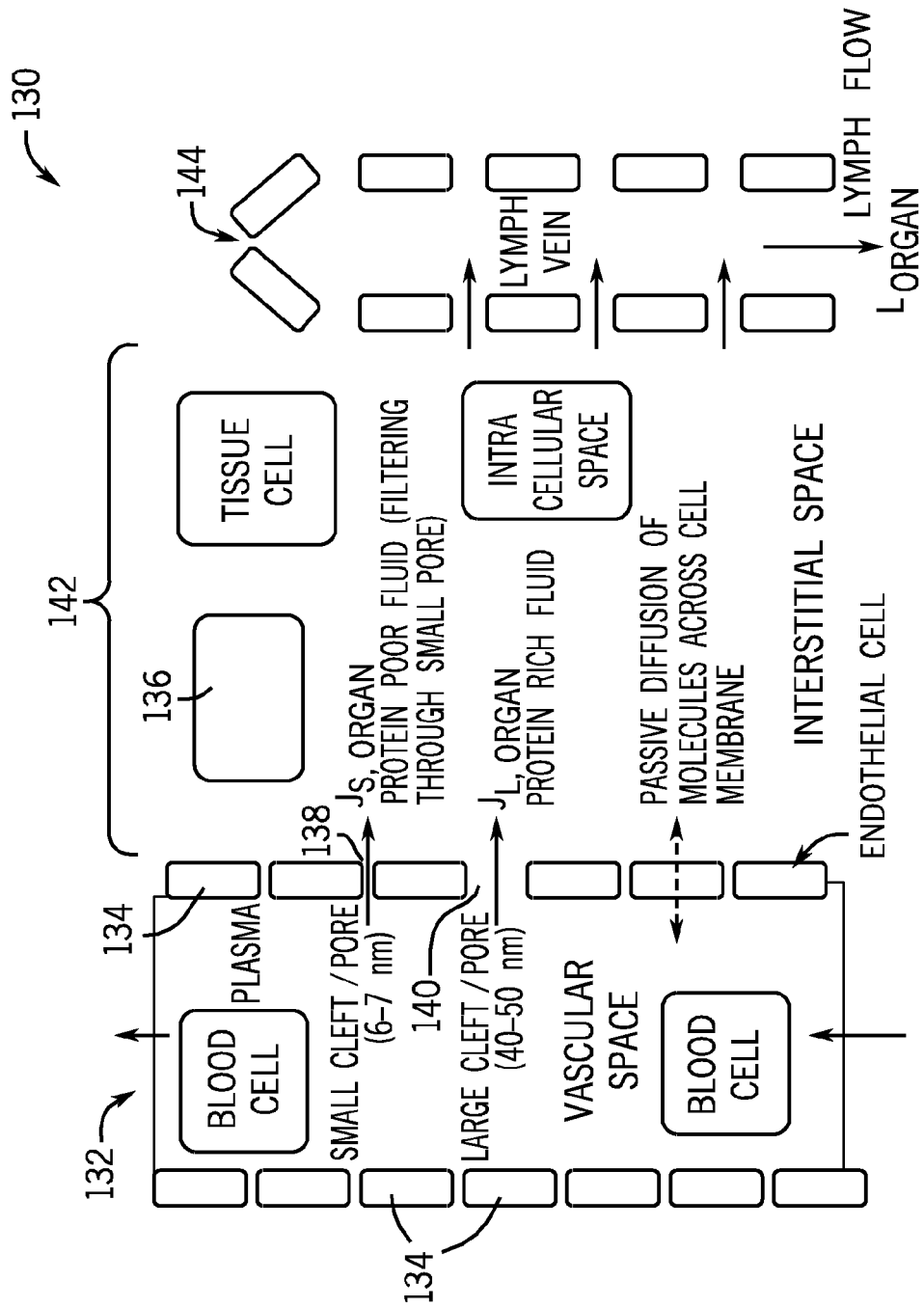
FIG. 7 depicts a schematic of the two-pore model, in accordance with an embodiment of the present disclosure.

Turning to FIG. 7, the two-pore model is discussed in relation to an implementation of the PBPK model. In FIG. 7, the vascular, interstitial, and intracellular space of general organ tissue 130 are depicted. The capillary 132 is lined with single layer endothelial cells 134 surrounded on the outside by a basement membrane. The capillary wall can have a total thickness of around 0.5 microns. The average internal radius of the capillary 132 may be 4 to 9 microns. It is generally understood that tissue cells 136 are generally within 20 to 30 microns of a capillary 132. The endothelia cells 134 are bound together by protein but have clefts, e.g., pores, between them that have a spacing distance of 6 to 7 nm. Smaller clefts 138 may be 6 to 7 nm in size and may accommodate protein poor fluids filtering through while larger clefts 140 may be 40 to 50 nm in size and may accommodate the passage of protein rich fluid. In addition, molecules may passively diffuse across the cell membranes of the endothelial cells 134 lining the capillary 132. The area of these intercellular clefts 138 may represent approximately $\frac{1}{1000}$ of the total surface area of the capillary walls. In different areas of the body, such as the brain, the liver, the intestinal membranes, the kidney, and so forth, the size and/or spacing of the clefts 138 may vary to accommodate the specialized functions of these organs.

The interstitial space 142 may contain collagen fiber bundles and proteoglycan filaments. These fiber bundles and filaments may create a gel-like environment. Diffusion through this gel-like environment may occur at a rate of about 95% of the rate in free fluid. In one implementation, there is assumed to be solvent (water) flow across both small, $J_{S,organ}$, and large, $J_{L,organ}$, pores. The sum of these two convective flows may be summed to equal the lymph flow, $L_{organ}$, for the organ tissue 130 to maintain its mass balance. Plasma proteins, like albumin which has a diameter of about 6 nm, will not pass through the small pores 138 but may pass through the large pores 140. This distinction may cause an osmotic pressure differential to be generated, which will lead to a slight flow reduction from the small pores 138 and a slight flow increase to the large pores 140. This flow reduction/increase is labeled $J_{iso,organ}$ and is described in equations 31-34 below which describe the convective flow:

$$\alpha_S + \alpha_L = 1 \quad (31)$$

$$J_{L,organ} = J_{iso,organ} + \alpha_L L_{organ} \quad (32)$$

$$J_{S,organ} = -J_{iso,organ} + \alpha_S L_{organ} \quad (33)$$

$$J_{iso,organ} = \alpha_L \alpha_S L_P S(\sigma_{S,organ} - \sigma_{L,organ})(\sigma_{v,organ} - \pi_{i,organ}).$$

The fractional hydraulic conductance for the small ($\alpha_S$) and large ($\alpha_L$) pores 138, 140 define what fraction of the lymph flow for an organ passes through the small pores 138 and large pores 140. The fluid recirculation flow rate, $J_{iso,organ}$, represents the flow rate through the large pores 140 into the interstitial space 142 returning through the small pores 138 when the lymph flow rate is zero. This recirculation is due to the difference in the osmotic pressure caused by the filtering of the small pores 138 relative to the large pores 140. With regard to typical trans-endothelial osmotic pressure differences, capillary pressure is typically about 17-25 mmHg, interstitial fluid pressure is typically between −4 to −1 mmHg, and average interstitial fluid pressure is typically about −3 mmHg. In other areas of the body, these values may vary. For example, in the brain the CSF may be at a pressure of about 10 mmHg and the brain's interstitial fluid may be around 4 to 6 mmHg. In the strong fibrous capsule around the kidney the pressure may be about 13 mmHg and the interstitial fluid may be around 6 mmHg.

With regard to the proteins typically seen in the plasma, these may include albumin 69 kDa (4.5 g/dl), globulins 140 kDa (2.5 g/dl) fibrinogen 400 kDa (0.3 g/dl). The average concentration of protein in the interstitial space 142 may be about 3 g/dl. Typically, osmotic pressure of the plasma may be about 28 mmHg, with 80% of this value being attributable to albumin. Interstitial fluid colloid osmotic pressure may be about 8 mmHg.

At the arterial end of the capillary 132, about 13 mm Hg of outward pressure moves about 0.5% of plasma to flow out of the capillaries 132 into the interstitial spaces 142. At the venous end of the capillary 132, about 7 mm Hg of inward pressure moves about 0.45% of the 0.5% back into the capillaries 132 with the remaining 0.05% going out the lymph vessels 144. On average there is 0.01 ml/min/mm Hg/100 grams of tissue of filtration to the lymph vessels 144. There is around 0.3 mmHg of average net pressure on average tissue. However, this pressure may vary by a factor of 100 among the various tissues of the body. The protein concentration in the interstitial space 142 of the: muscles is 1.5 g/dl, adipose is 1 g/dl, subcutaneous tissues is 2 g/dl, intestine is 3-4 g/dl, liver is 6 g/dl, and average tissue is 2 g/dl.

Referring to equation 34, the reflection coefficient, σ, represents the fraction of the solute that will be reflected by a membrane due to the size of the solute molecule relative to the size of the membrane pores. Solute molecules larger than the hole will always reflect while those solute molecules that are smaller than the hole will still be reflected at some rate corresponding to the relative size of the solute molecule to the hole. In general the reflection coefficient for a probe for a given circular pore radius may be described, in one implementation, by the equation:

$$\lambda = \frac{r_{probe}}{r_{pore}} \begin{cases} \lambda < 1 & \sigma = 1 - \frac{(1-\lambda)^2(2-(1-\lambda)^2)\left(1 - \frac{1}{3}\lambda\right)}{1 - \frac{1}{3}\lambda + \frac{2}{3}\lambda^2} \\ \lambda \geq 1 & \sigma = 1 \end{cases} \quad (35)$$

where θ varies with λ in accordance with the curve depicted in FIG. 8.

As the size of solute molecule increases the microvascular walls generally become effectively impermeable to macromolecules by a passive diffusion mechanism. Two factors lead to this effective impermeability by passive diffusion. First, the diffusion coefficient of a molecule decreases as the molecular size increases. Second, the relative partitioning of the molecule in water versus the nonpolar environment of the cell membrane tends to preclude passive diffusion of large molecules. In particular, macromolecules, in order to maintain their solubility in the aqueous environment, tend to have more hydrophilic content to them and thus favor the aqueous environment versus the non polar cell membrane environment.

In view of the foregoing discussion, the flow of the probe from the vascular free to the interstitial free compartment in one implementation of a PBPK model may be described by equations 36-38 as follows:

$$J_{vi,organ} = \lfloor J_{L,organ}(1 - \sigma_{L,organ}) + J_{S,organ}(1 - \sigma_{S,organ}) \rfloor \quad (36)$$

$$C_{vf,organ} + \left[\frac{\alpha_L P_{eL}}{e^{P_{eL}} - 1} + \frac{\alpha_S P_{eS}}{e^{P_{cs}} - 1}\right] PS_{vi,organ}\left(C_{vf,organ} - \frac{C_{if,organ}}{R_{vi,organ}}\right)$$

$$P_{eL} = \frac{J_{L,organ}(1 - \sigma_{L,organ})}{\alpha_L PS_{vi,organ}} \quad (37)$$

$$P_{eS} = \frac{J_{S,organ}(1 - \sigma_{S,organ})}{\alpha_S PS_{vi,organ}}. \quad (38)$$

The preceding discussion and equations relate to the construction and function of one implementation of a PBPK model and is not intended to be limiting in any manner. As will be appreciated, in other implementations a PBPK model may be adapted to include various cell types, such as endothelial cells, stem cells and/or multiple cell types associated with a given organ tissue. In addition, in other implementations bacterial cells could be included in a PBPK model by including the bacterial cell compartments at different locations, such as in the chyme of the GI tract or in an infected organ tissue. Such an implementation may be useful where the bacterial cells are the target of the probe under review.

PBPK models as discussed above may process various inputs, such as the physiology and anatomy parameters 16, the biomarker properties 18, the probe properties, 20, run parameters 22, and so forth (see FIG. 1). The physiology and anatomy related parameters 16 include the anatomical, physiological, and cellular parameter data for the organism being modeled, such as plasma flow rates, lymph flow rates, and organ tissue volumes. Such physiology and anatomy related parameters 16 may be measured for a particular species being modeled and are typically independent of the probe properties 20. The physiology and anatomy related parameters 16 may also include the names, concentration, and sub-cellular locations of enzymes that bind, transport, or biotransform the probe.

In one implementation, organ mass, organ volume, plasma flow, and other physiological and anatomical parameters 16 were collected for three species that include mouse, rat, and human. As will be appreciated, variance exists for the physiological and anatomical parameters 16 within a species due to sex, age, and environmental factors. Further, within an individual, there can be variance in certain parameters, such as the flow parameters, depending upon the individual's state (e.g. at rest) and the surrounding environment (e.g. temperature).

The mass in grams for each of the organ tissues defined in the described implementation of the PBPK model is presented in Table 1. These mass values were compiled from the existing literature. The mass of the wet organ tissues does not include any contribution from blood that would be located in the organ's micro-vascular space. The mass of the blood is the sum of plasma and red blood cells for the whole body. In other implementations, other organs or structures, such as the pancreas, the thyroid, and/or tumors may also be included in this and the subsequent tables.

TABLE 1

| | Wet Tissue Weight (grams) | | | Mass Fraction | | |
|---|---|---|---|---|---|---|
| Tissue | Mouse | Rat | Human | Mouse | Rat | Human |
| Blood | 1.7 | 16.9 | 5,900 | 0.0741 | 0.0698 | 0.0869 |
| Lung | 0.12 | 1.5 | 470 | 0.0052 | 0.0062 | 0.0069 |
| Heart | 0.08 | 1 | 330 | 0.0035 | 0.0041 | 0.0049 |
| Muscle | 10 | 109 | 30,000 | 0.4359 | 0.4503 | 0.4419 |
| Skin | 2.9 | 31.5 | 3,300 | 0.1264 | 0.1301 | 0.0486 |
| Adipose | 0.51 | 18.5 | 12,500 | 0.0222 | 0.0764 | 0.1841 |
| Bone | 3.47 | 38 | 10,500 | 0.1513 | 0.1570 | 0.1547 |
| Brain | 0.36 | 1.8 | 1,400 | 0.0157 | 0.0074 | 0.0206 |
| Kidney | 0.32 | 2 | 310 | 0.0139 | 0.0083 | 0.0046 |
| Liver | 1.75 | 10 | 1,800 | 0.0763 | 0.0413 | 0.0265 |
| Spleen | 0.1 | 0.75 | 180 | 0.0044 | 0.0031 | 0.0027 |
| GI Tract | 1.63 | 11.1 | 1,200 | 0.0711 | 0.0459 | 0.0177 |
| Total | 22.94 | 242.05 | 67,890 | 1.000 | 1.000 | 1.000 |

In one implementation, the PBPK model may be configured to accept a total body mass parameter and then calculate the mass of each organ tissue using the mass fraction data presented in Table 1 or a similar set of mass fraction data. In one such implementation, a total body mass of 20, 250, and 70,000 g is used for the mouse, rat, and human respectively. Therefore, the mass of each organ tissue can be slightly higher or lower from that given in the table depending upon what total body mass is used in the calculation.

The fraction of an organ's total volume that is divided between the vascular, interstitial and intracellular spaces may be derived from the literature or other sources. An example of one such division of organ tissue volume is presented in Table 2. In one embodiment it is assumed that these fractions are the same across the species of interest, such as for human, rat, and mouse. The vascular space may be further subdivided into the plasma and the intra-red blood cell spaces. In one implementation, it is assumed that the packed red blood cell volume (i.e. hematocrit) of blood is around 0.4 for a man. Thus the vascular space for each organ tissue is subdivided into 60% plasma space and 40% into intra-RBC space in such an implementation.

TABLE 2

| | Volume Fraction | | |
|---|---|---|---|
| Tissue | Vascular | Interstitial | Intracellular |
| Blood | 1 | 0 | 0 |
| Lung | 0.1 | 0.3 | 0.6 |
| Heart | 0.05 | 0.14 | 0.81 |
| Muscle | 0.02 | 0.13 | 0.85 |
| Skin | 0.0679 | 0.33 | 0.6021 |
| Adipose | 0.0146 | 0.24 | 0.7454 |
| Bone | 0.1 | 0.186 | 0.714 |
| Brain | 0.0799 | 0.2 | 0.7201 |
| Kidney | 0.1 | 0.34 | 0.56 |
| Liver | 0.1 | 0.2 | 0.7 |
| Spleen | 0.0979 | 0.2 | 0.7021 |
| GI Tract | 0.02 | 0.17 | 0.81 |

In certain embodiments of a PBPK model, a significant portion of the total body blood supply is distributed between the various vascular compartments of the organ tissues. In such embodiments, the remaining blood is assumed to be located in major arteries and veins of the body and is defined as the blood compartment. In one implementation, it is assumed that the mass fraction of blood that remains in this blood compartment is 0.4 for mouse, 0.39 for rat, and 0.6 for human. The main reason for the large difference in the blood pool between the human (0.6) and the other two species (0.39-0.4) is due to differences in the mass fraction of skin. The skin has a significantly larger fraction of vascular space as seen in Table 2 and the mass fraction of skin is significantly higher in mouse and rat relative to man as seen in Table 1.

The partitioning of a probe between tissues is dependent upon how hydrophobic the agent is and the relative volumes of the organic and aqueous phases of the tissue. The fraction of a tissue that is water and the fraction that is organic are presented in Table 3. The data from this table was generated using measured and published values for the fraction of water of organ tissues. In one implementation, the organic fraction is assumed to be one minus the water fraction. In one embodiment, the measured water fraction of erthrocytes was set to 0.676 and 0.662 for human and rat respectively. After accounting for the major plasma proteins albumin, globulins, and fibrinogen, the water fraction of blood plasma was set to 0.945 in one embodiment. The water fraction for the interstitial space of the organ tissues was estimated based on local plasma protein concentrations. The rate of lymph flow controls the concentration of plasma proteins within the interstitial space of a particular organ. Finally, the intracellular water fraction was calculated using published whole organ values after removing the contribution from the interstitial space. The aqueous volume fraction of the bile was assumed to be 0.3. In Table 3, the blood interstitial estimate corresponds to the blood plasma while the blood intracellular estimate corresponds to the intra-RBC blood component. In implementations modeling a tumor, the tumor values may be assumed to be the same as or similar to those for muscle.

TABLE 3

| | Density | Aqueous Fraction | | Organic Fraction | |
|---|---|---|---|---|---|
| Tissue | (g/cm$^3$) | Interstitial | Intracellular | Interstitial | Intracellular |
| Blood | 1.065 | 0.942 | 0.6760 | 0.058 | 0.3240 |
| Lung | 1.021 | 0.966 | 0.7020 | 0.034 | 0.2980 |
| Heart | 1.022 | 0.966 | 0.7467 | 0.034 | 0.2533 |
| Muscle | 1.024 | 0.967 | 0.7228 | 0.033 | 0.2772 |
| Skin | 1.036 | 0.915 | 0.4970 | 0.085 | 0.5030 |
| Adipose | 0.943 | 0.978 | 0.1500 | 0.022 | 0.8500 |
| Bone | 1.581 | 0.966 | 0.3105 | 0.034 | 0.6895 |
| Brain | 0.979 | 0.985 | 0.7330 | 0.015 | 0.2670 |
| Kidney | 1.023 | 0.966 | 0.6526 | 0.034 | 0.3474 |
| Liver | 1.030 | 0.937 | 0.6304 | 0.063 | 0.3696 |
| Spleen | 1.023 | 0.966 | 0.7155 | 0.034 | 0.2845 |
| GI Tract | 1.025 | 0.949 | 0.7098 | 0.051 | 0.2902 |

Table 3 also presents the estimated densities of the wet organ tissue after the blood has been removed. The density was calculated assuming water has a density of 1.0 g/cm$^3$ and the organic fraction was assumed to have a density of 1.1 g/cm$^3$. An exception to this estimation method was used for adipose, brain, blood, and bone tissues. For adipose tissue, the organic fraction was assumed to have a density of 0.9 g/cm$^3$ since it is mostly triglycerides. The brain has a substantial fat content (i.e. myelin, white matter) which gives it a lower than expected density value. The blood density was calculated based on blood plasma having a density of 1.025 g/cm$^3$ and red blood cells having a density of 1.125 g/cm$^3$. With a 0.4 fraction of red blood cells, the density of whole blood becomes 1.065 g/cm$^3$. The density of bone tissues was calculated based on compact bone having a density of 1.9 g/cm$^3$ and marrow within the porous bone having a density of 1.06 g/cm$^3$. Cortical bone represents nearly 80% of the skeletal mass and 30% of this cortical bone is porous. Trabecular (or cancellous) bone represents 20% of the skeletal mass and 70% of it is porous. This gives an average porous fraction of 0.38. Thus the average bone density is assumed to be 1.5808 g/cm³ (0.38*1.06+0.62*1.9) in one embodiment.

From the mass fractions of the various organ tissues presented in Table 1 and the organ tissue densities presented in Table 3, the average body density can be estimated to be 1.084, 1.081, and 1.069 g/cm³ for mouse, rat, and man respectively. This estimated density assumes no air is present in the lungs. With the lungs at maximum capacity of 5.8 L for an adult man, the average body density is reduced to 0.982 g/cm³.

The plasma flow rate in milliliters per minute within the vasculature of each organ tissues defined in the presently described PBPK model is presented in Table 5. These plasma flow rates were compiled from published sources. The total column at the bottom of the table is the sum of the plasma flow rates for each organ excluding the blood, lung, and liver. The plasma flow to the liver is fed by the hepatic artery and the portal vein. The portal vein receives blood from the venous outflow of the gastrointestinal (GI) tract and spleen. Therefore, the liver plasma flow rate is the sum of the flow rates of hepatic, spleen, and GI tract. The blood and lung are excluded from the total because, in one embodiment of the PBPK model, the blood and lung organs receive 100% of the cardiac output. In PBPK model implementations where a tumor is also being modeled, the plasma flow rate to the tumor may be assumed to be ⅓ of the proportional plasma flow rate to muscle tissue.

TABLE 4

| Tissue | Plasma Flow Rate (ml/min) | | | Fraction Cardiac Output | | |
|---|---|---|---|---|---|---|
| | Mouse | Rat | Human | Mouse | Rat | Human |
| Blood | 7.361 | 67.97 | 5,190 | 1.0000 | 1.0000 | 1.0000 |
| Lung | 7.361 | 67.97 | 5,190 | 1.0000 | 1.0000 | 1.0000 |
| Heart | 0.34 | 3.14 | 240 | 0.0462 | 0.0462 | 0.0462 |
| Muscle | 1.27 | 11.7 | 750 | 0.1725 | 0.1721 | 0.1445 |
| Skin | 0.43 | 4 | 300 | 0.0584 | 0.0588 | 0.0578 |
| Adipose | 0.371 | 3.4 | 260 | 0.0504 | 0.0500 | 0.0501 |
| Bone | 0.36 | 3.33 | 250 | 0.0489 | 0.0490 | 0.0482 |
| Brain | 0.75 | 6.9 | 700 | 0.1019 | 0.1015 | 0.1349 |
| Kidney | 1.77 | 16.4 | 1,240 | 0.2405 | 0.2413 | 0.2389 |
| Liver | 2.07 | 19.1 | 1,450 | 0.2812 | 0.2810 | 0.2794 |
| Hepatic | 0.39 | 3.6 | 273 | 0.0530 | 0.0530 | 0.0526 |
| Spleen | 0.11 | 1 | 77 | 0.0149 | 0.0147 | 0.0148 |
| GI Tract | 1.57 | 14.5 | 1,100 | 0.2133 | 0.2133 | 0.2119 |
| Total | 7.361 | 67.97 | 5,190 | 1.0000 | 1.0000 | 1.0000 |

In one implementation, the PBPK model accepts a total cardiac mass parameter and then calculates the plasma flow rate of each organ tissue using the fraction cardiac output data presented in Table 4. For example, a total cardiac output flow of 8, 74, and 5,600 ml/min may be used for the mouse, rat, and human respectively. Therefore, the plasma flow rate of each organ tissue can be slightly higher or lower from that given in Table 4 depending upon what total cardiac output is used in the calculation.

In one implementation, the lymph flow rates may be calculated by tuning the PBPK model to the albumin concentrations found in the various organ tissues. The concentration of albumin, as determined from various published source, is presented in Table 5.

TABLE 5

| Tissue | Interstitial Albumin Conc. Molar | Interstitial Albumin Conc. (g/dl) | Fraction Total Albumin |
|---|---|---|---|
| Blood (plasma | 5.73E−04 | 3.8 | 0.485 |
| Lung | 1.84E−04 | 1.2 | 0.006 |
| Heart | 1.84E−04 | 1.2 | 0.002 |
| Muscle | 1.67E−04 | 1.1 | 0.156 |
| Skin | 6.99E−04 | 4.6 | 0.180 |
| Adipose | 6.70E−05 | 0.4 | 0.052 |
| Bone | 1.84E−04 | 1.2 | 0.056 |
| Brain | 0 | 0 | 0.000 |
| Kidney | 1.84E−04 | 1.2 | 0.005 |
| Liver | 4.67E−04 | 3.1 | 0.040 |
| Spleen | 1.84E−04 | 1.2 | 0.002 |
| GI Tract | 3.49E−04 | 2.3 | 0.017 |

Albumin is a major plasma protein representing about 60% of the total plasma protein content. It is a 585 amino acid residue protein with a molecular weight of 66,500 daltons and contains over 97 negative charges. The albumin concentration in blood plasma ranges in humans from 3.9e-4 to 7.5e-4 M. Albumin has no means to passively transport across a lipid membrane. As presented earlier, the two pore model has both small and large pores as implemented in one embodiment of the PBPK model. In one such implementation, the small pores or clefts between the capillary endothelial cells are defined to be 35 angstroms in radius for all tissues except the brain which is set to 0.1 microns. In this implementation, the large pores are defined to be 230 angstroms in radius for all organ capillary except for brain which is set to 0 microns. In this example, the hydrodynamic radius of albumin is about 30 angstroms so it is 95% reflected from the small pores but passes freely (<5% reflection) through the large pores.

In this example, running the model and tuning the lymph flow rates to match the albumin concentrations in the various interstitial compartments defined the fraction of large pores to be 0.034 and the fraction of small pores to be 0.966. This parameter ended up controlling the total lymph flow rate which is about 2 ml/min in a human adult male at rest.

In this example, other parameters set in the PBPK model to tune the lymph flows included: temperature=37° C., capillary radius=5.3 microns, tissue cell radius=25 microns, RBC radius=3.63 microns, endothelial cell thickness=1 micron, interstitial thickness=3 microns, permeability PI distance=2 microns, permeability IC distance=capillary radius+endothelial cell thickness+(interstitial thickness/2), permeability IC distance=(interstitial thickness/2)+tissue cell radius, permeability PR distance=RBC radius+(capillary radius/2), permeability bile distance=tissue cell radius, transendothelial osmotic pressure difference=14.06 mmHg, and hydraulic conductivity capillary wall=1.3E-07 cm/mmHg/min. The lymph flow rates observed in one implementation by tuning the PBPK model to albumin tissue concentrations using these parameters are presented in Table 7.

TABLE 7

| | Lymph Flow Rate (ml/min) | | |
|---|---|---|---|
| Tissue | Mouse | Rat | Human |
| Blood | na | na | na |
| Lung | 8.4E−06 | 1.6E−04 | 4.5E−02 |
| Heart | 2.3E−06 | 4.5E−05 | 1.4E−02 |
| Muscle | 1.8E−04 | 2.6E−03 | 5.2E−01 |
| Skin | 1.1E−04 | 1.6E−03 | 4.3E−02 |
| Adipose | 1.8E−06 | 3.5E−04 | 7.0E−01 |
| Bone | 2.1E−04 | 3.1E−03 | 6.4E−01 |

TABLE 7-continued

| | Lymph Flow Rate (ml/min) | | |
|---|---|---|---|
| Tissue | Mouse | Rat | Human |
| Brain | na | na | na |
| Kidney | 2.4E-04 | 6.2E-04 | 2.9E-02 |
| Liver | 2.0E-04 | 6.7E-04 | 5.7E-02 |
| Spleen | 1.9E-05 | 1.1E-04 | 1.7E-02 |
| GI Tract | 8.0E-05 | 3.5E-04 | 8.8E-03 |
| Total | 1.1E-03 | 9.6E-03 | 2.07 |

The brain does not have lymph veins but the CSF may be modeled in a similar manner. Published CSF flow rates for mouse, rat, and human to be 3.7E-04, 2.8E-03, and 0.347 respectively. These and other flow rates for special compartments are provided in Tables 8 and 9 which, respectively, describe volumes and flow rates that may be employed for the special compartments in one implementation of the PBPK model.

TABLE 8

| | Volume (ml) | | |
|---|---|---|---|
| | Mouse | Rat | Human |
| Bile | 0.046 | 0.31 | 56 |
| Chyme | 1.194 | 9.63 | 1,039 |
| Feces | 0.185 | 1.49 | 161 |
| Urine | 0.320 | 2.00 | 310 |

TABLE 9

| | Flow Rate (ml/min) | | |
|---|---|---|---|
| | Mouse | Rat | Human |
| Brain CSF | 3.7E-04 | 2.8E-03 | 0.347 |
| Bile | 1.4E-03 | 1.6E-02 | 0.243 |
| Chyme | 1.4E-02 | 1.1E-01 | 4.37 |

With regard to the two-pore model that may be employed in certain embodiments of the PBPK model, Table 10 presents an example of input parameters related to pore size that may be employed in certain implementations of the PBPK model.

TABLE 10

| Tissue | Endothelial Cleft/Pore Percent Area | Small Pore Radius Angstroms | Large Pore Radius Angstroms | Fraction of Pores that are Large | Tissue Cell Radius Microns | Cell Plasma Membrane Surface Area Multiplier |
|---|---|---|---|---|---|---|
| Blood | 0.0 | 0 | 0 | 0 | 3.6 | 1 |
| Lung | 0.3 | 35 | 230 | 0.034 | 15 | 1 |
| Heart | 0.3 | 35 | 230 | 0.034 | 20 | 1 |
| Muscle | 0.3 | 35 | 230 | 0.034 | 20 | 1 |
| Skin | 0.3 | 35 | 230 | 0.034 | 15 | 1 |
| Adipose | 0.3 | 35 | 230 | 0.034 | 20 | 1 |
| Bone | 3.0 | 50 | 230 | 0.034 | 15 | 1 |
| Brain | 0.1 | 0.1 | 0.1 | 0 | 20 | 1 |
| Kidney | 3.0 | 35 | 230 | 0.034 | 15 | 6 |
| Liver | 6.0 | 75 | 230 | 0.034 | 11 | 6 |
| Spleen | 6.0 | 75 | 230 | 0.034 | 15 | 1 |
| GI Tract | 3.0 | 50 | 230 | 0.034 | 15 | 6 |
| Pancreas | 0.3 | 35 | 230 | 0.034 | 15 | 1 |
| Thyroid | 0.3 | 35 | 230 | 0.034 | 15 | 1 |
| Tumor | 0.3 | 35 | 230 | 0.034 | 15 | 1 |

In addition, the physiology and anatomy parameters 16 utilized by the PBPK model may account for the pH of the various compartments, which may be a factor when a molecule includes ionizable groups. Examples of pH values that may be provided and utilized in one embodiment of the PBPK model include: $pH_{plasma,\ liver}=7.38$, $pH_{plasma,\ other}=7.4$, $pH_{intrarbc}=7.0$, $pH_{interstitial}=7.35$, $pH_{intracellular}=7.0$, $pH_{bile}=7.0$, $pH_{small\ intestine,\ beginning}=5.4$, $pH_{small\ intestine,\ end}=7.5$, and $pH_{urine}=4.5$-$8.0$.

Likewise, other parameters may be accounted for in implementations of a PBPK model. These factors may include, but are not limited to the examples set forth in Table 11 below.

TABLE 11

| glomerular filtration pore radius | 40 angstroms |
|---|---|
| glomerular kidney cardiac output filtration fraction | 0.2 |
| BBB passive diffusion fraction | 1 |
| hepatocyte fraction canalicular membrane | 0.1 |
| organ bile flow rate | 0.00139 ml/min |
| organ digestive tube transition time | 88 minutes |
| aqueous volume fraction bile | 0.3 |
| volume bile per gram liver | 0.03 |
| volume chyme per gram GI tract | 0.84 |
| volume kidney tubules per gram kidney | 0.44 |
| proximal tubule flow multiple of glomular filtration rate | 0.35 |
| proximal tubule surface area | 1570 cm$^2$ |
| proximal tubule radius | 23 microns |
| small intestines surface area | 11400 cm$^2$ |
| plasma volume fraction in blood | 0.6 |
| mass fraction porous bone mass | 0.38 |
| capillary radius | 5.3 microns |
| endothelial cell thickness | 1.0 microns |
| interstitial thickness | 3.0 microns |
| tran-endothelial osmotic pressure difference | 14.06 |
| hydraulic conductivity at capillary wall | 1.3e-7 |
| endosome radius | 0.05 microns |
| average thickness of golgi ER | 0.025 microns |
| early endosome volume fraction of cell | 0.01 |
| golgi-ER-Lyosome volume fraction of cell | 0.15 |
| cytosol, nucleus, mitochondria, peroxisome volume fraction of cell | 0.84 |

The preceding describes the PBPK model and various physiological and anatomical parameters 16 that may be provided as inputs to such a PBPK model. Probe properties 20 may also be provided as inputs to such a PBPK model. Such probe properties 20 may include the relevant physical-chemical property information for the exogenous molecule or molecules being assessed. For example, such probe properties 20 may include the molecular weight of the probe, the hydrodynamic radius ($R_h$), miLog P, LogD (pH 7.4), logP/logD, probe-plasma protein binding, probe clearance rates, biomarker-probe binding rate and/or strength, and/or the diffusion coefficient associated with the probe. The probe properties 20 may also include biochemical properties of the probe including possible metabolites of the probe and their properties as well as known enzymes for which the probe is a substrate. The term enzyme may be defined as a protein that can either bind, transport, or biotransform the substrate molecule, i.e., the probe. The kinetic rate parameters for the enzyme-molecule complex may also be specified in the probe properties 20.

For example, in one implementation, the composition 99mTc-DTPA may be used as a probe to evaluate a PBPK model. The 99mTc-DTPA composition is considered to be passive with no specific binding, active transport processes, and no biotransformations and can undergo passive fluid phase endocytosis. In such an example, the PBPK model may be provided input parameters for 99mTc-DTPA that include: molecular weight: 491 g/mole; hydrodynamic radius ($R_h$): 5.8 angstroms; miLogP: −5.4; LogD (pH 7.4): −15.6; and diffusion coefficient: 5.6E-06 cm2/sec.

While the inputs to the PBPK model may include a physiology and anatomy parameters 16 and probe properties 20 as discussed above, the output of the PBPK model may include a predicted biodistribution (such as a time-concentration curve or time-activity curve (TAC)) for each combination of parameter values, or experimental factors, under consideration. For example, Table 12 provides an example of different variables and corresponding variable values that may be used in one implementation to assess a probe, with a predicted biodistribution 14 being generated for each combination of variable values.

TABLE 12

| Variable | Range |
| --- | --- |
| Probe Molecular Weight | 500, 2000, 10000, 40000 g/mol |
| Probe LogD | 3, 1, −1, −2.5, −6 |
| Probe Specific Plasma Protein Binding | No, Yes ($K_d$ = 50 μM and $k_{on}$ = 1e5 $M^{-1}$ $sec^{-1}$) |
| Active Biliary Probe Clearance | No, Yes |
| Biomarker Location | Cell Membrane<br>Cell Cytosol |
| Biomarker Concentration, Local | 10 nm, 100 nM, 1μ> |
| Biomarker Concentration, Organ | 2% ductal involvement:<br>9 pM, 90 pM, 900 pM<br>10% ductal involvement:<br>40 pM, 400 pM, 4 nM<br>15% ductal involvement:<br>70 pM, 700 pM, 7 nM |
| Biomarker Binding Affinity ($K_d$) | 0.1 nM, 1 nM, 10 nM, 100 nM |
| Biomarker Binding On Rate ($K_{on}$) | 1e3, 1e4, 1e5, 1e6 $M^{-1}$ $sec^{-1}$ |

In addition, the injected dose of the probe, the location at which the probe is administered, and the various time points (such as 1 hour, 2 hour, 3, hour, and so forth) for which a biodistribution is to be generated may be specific, such as in the run parameters 22. Each of these additional variables may also constitute an experimental factor such that a predicted biodistribution is generated for each of the combinations of factors being assessed, i.e., each actor constitutes a dimension in the analysis. In this manner, hundreds, thousands, tens of thousands, or more biodistributions, each representing a different combination of biomarker-probe conditions, may be calculated and assessed.

As discussed with regard to FIG. 1, some or all of the predicted biodistributions may be provided as inputs to an imager model that simulates the physics of a particular imaging modality. In addition, the imager model may be provided phantom parameters 28 consistent with the physiology and anatomy parameters 16 used to generate the predicted biodistributions 14. The phantom parameters 28, in one embodiment, may be geometrically modeled from the physiology and anatomy parameters 16 and represent the three-dimensional anatomical structure of a simulated patient. In one embodiment, the imager simulation maps the predicted biodistributions, such as time-concentration curves or time-activity curves for each tissue to their corresponding spatial location in a digital human (or other species) phantom, such as a Zubal virtual phantom. In one embodiment, the imager model may simulate scanner characteristics corresponding to a GE DST scanner operating in 2-D mode. The simulation software may use this scanner information along with details of the imaging protocol to be simulated (radiolabel half-life, acquisition start time, duration, and so forth) to generate sinograms with realistic noise for the imaging modality in question, such as PET, which are then reconstructed using filtered back projection to provide the images that can then be analyzed for probe uptake.

Because the imager model is based on the underlying physics of the imaging modality in question, the imager model may also represent the noise, scattering, spillover, image-processing effects and other imaging conditions typically observed for that imaging modality. For example, in a PET simulation, the noise level of the PET measurement may be about 15%. Thus, the output simulated images 30 represent not only the simulated anatomy and probe signal (derived from the phantom parameters 28 and predicted biodistribution 14), but also noise and other conditions normally seen. This allows for a complete in silico simulation that takes the chemical structure of the probe as input and predicts the final image of a human subject in the clinic.

As discussed with regard to FIG. 1, a small number (such as less than 10, 20, or 50) of simulated images 30 may be used, in certain embodiments, to derive set points or thresholds 34 that may be used to evaluate each of the predicted biodistributions 14. The derivation of the scoring thresholds 34 may be based on various criteria. For example, one criterion might be that there is enough contrast between the organ highlighted by the probe (such as the pancreas) and the surrounding tissues (small intestines, kidneys, stomach, liver, spleen) such that there is a strong enough signal to delineate the organ of interest from the background tissues. This criterion may be less important in simulated imaging modalities, such as PET/CT, where aspects of the imaging modality (such as CT in this example) may be used to distinguish anatomical features. Another criterion might in deriving the scoring thresholds 34 might be the ability to detect the small change in signal due to the lesions or other tissue abnormalities compared to background variability in a population of healthy control subjects. Based on these criteria, numeric values can be derived based on the simulated images 30 that may then be used to score the predicted biodistributions.

For example, in one embodiment, scoring thresholds 34 were derived from simulated images 30 depicting pancreatic tissue. Table 13 describes these derived scoring thresholds 34 and the biodistribution classifications to which they correspond. In Table 13, the ratios are calculated using biodistribution % ID/g.

TABLE 13

| Feasibility-Classification | (Patient's Pancreas Uptake)/ (Control Population Pancreas Uptake) Ratio | TBR: Pancreas to Background Tissue Uptake Ratio |
|---|---|---|
| Not Feasible | <1.25 | <2 |
| Maybe (High Risk) | 1.25-1.67 | 2-3.5 |
| Feasible | >1.67 | >3.5 |

In one such implementation, the criteria for the "Not Feasible" category may be selected to minimize or reduce the number of false negatives (i.e., where the assessment predicts a failure when in reality it would work). Thus, the criteria that defined the "Not Feasible" category may be selected to be very close to the measurement noise level in the simulated images 30. In certain embodiments, it may not be possible to define the noise level for all imaging situations. In such embodiments, the scoring thresholds 34 may be based on previous measurements with or without a small safety margin.

The derived scoring thresholds 34 may be used to score the predicted biodistributions 14. In one implementation, the PBPK model and its input parameters may be used to calculate the percent injected dose per gram tissue (% ID/g) and the corresponding ratios that are compared to the scoring thresholds 34. Such an embodiment may be useful where the use of ratios reduces linear biased errors in both experimental and calculated data.

Figure 9:
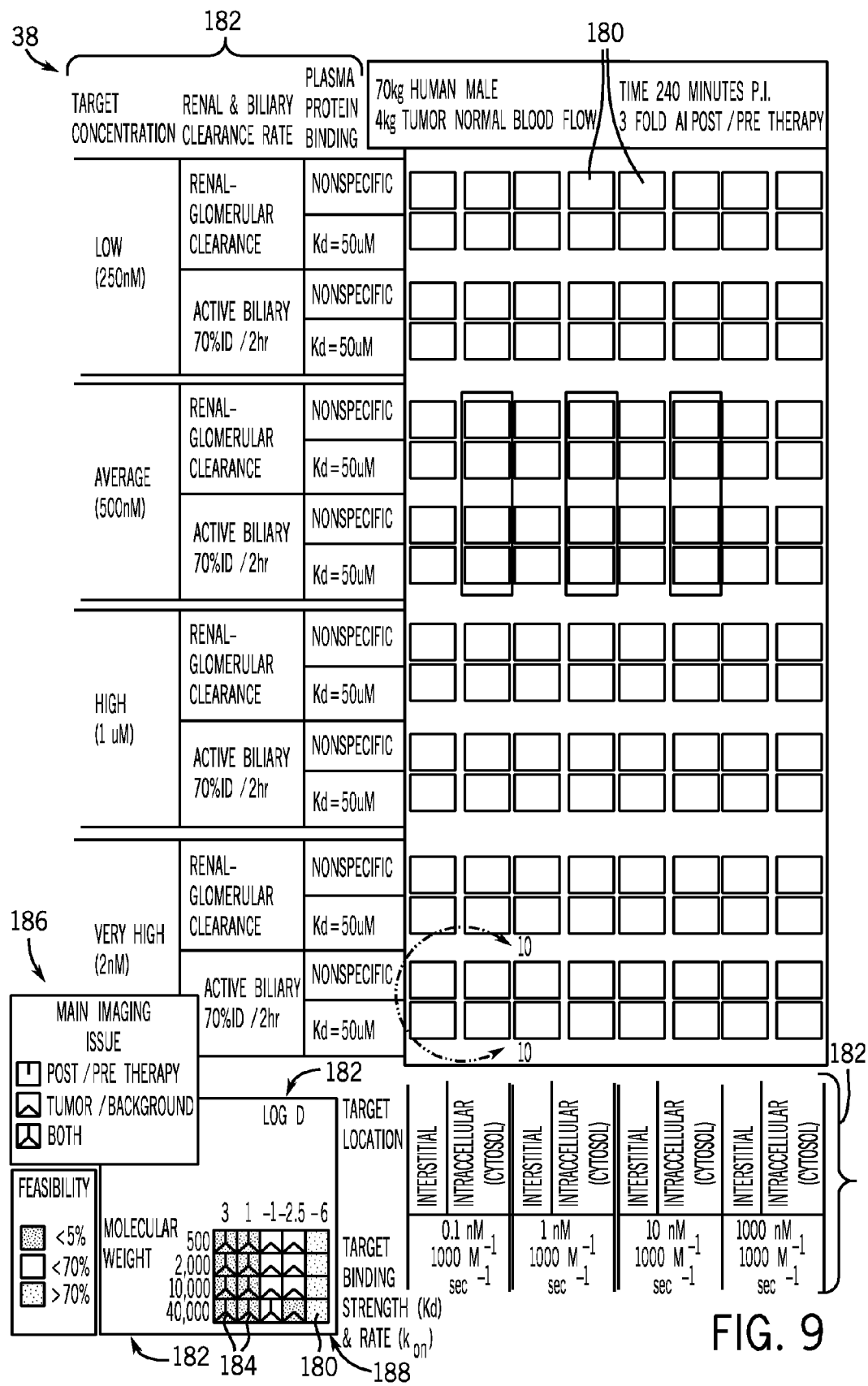
FIG. 9 depicts an imageability map, in accordance with an embodiment of the present disclosure.
Figure 10:
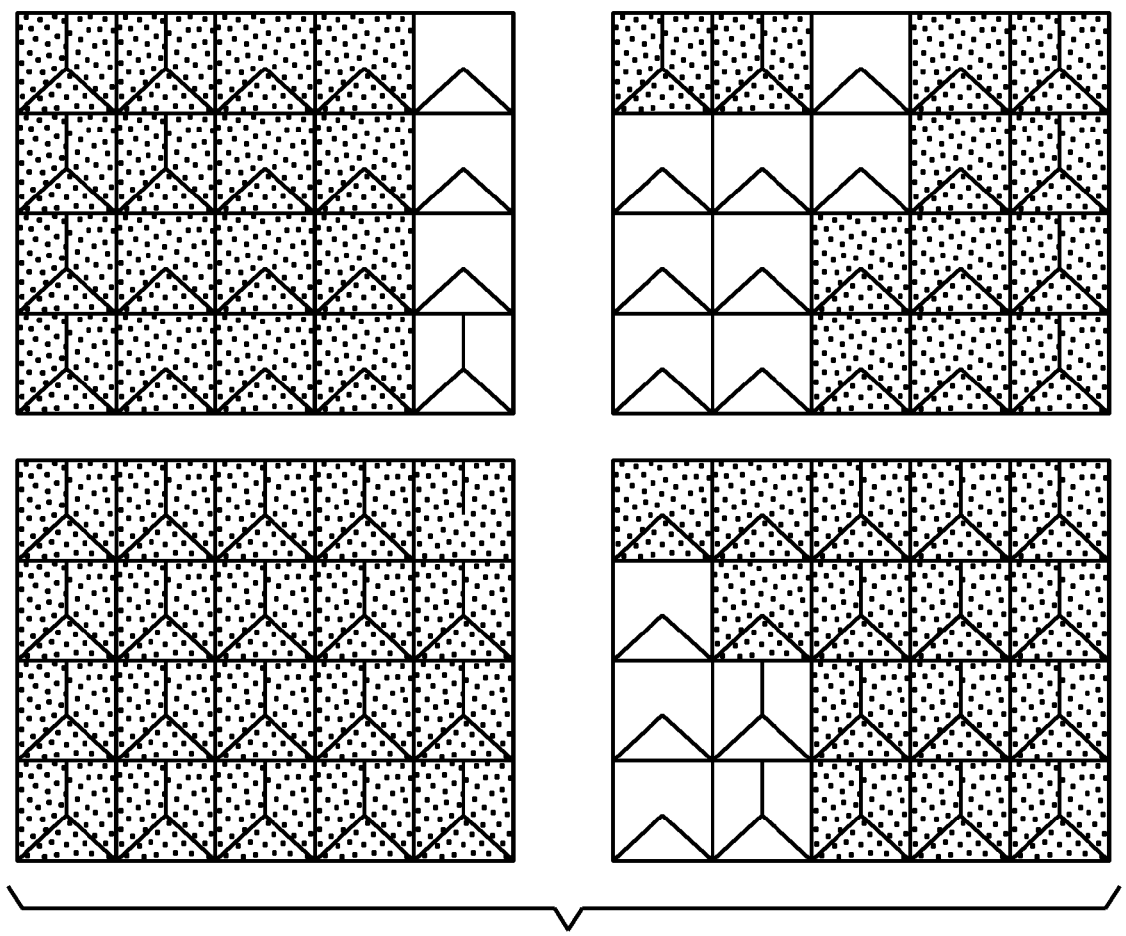
FIG. 10 depicts the inset of FIG. 9 in greater detail.
Figure 11:
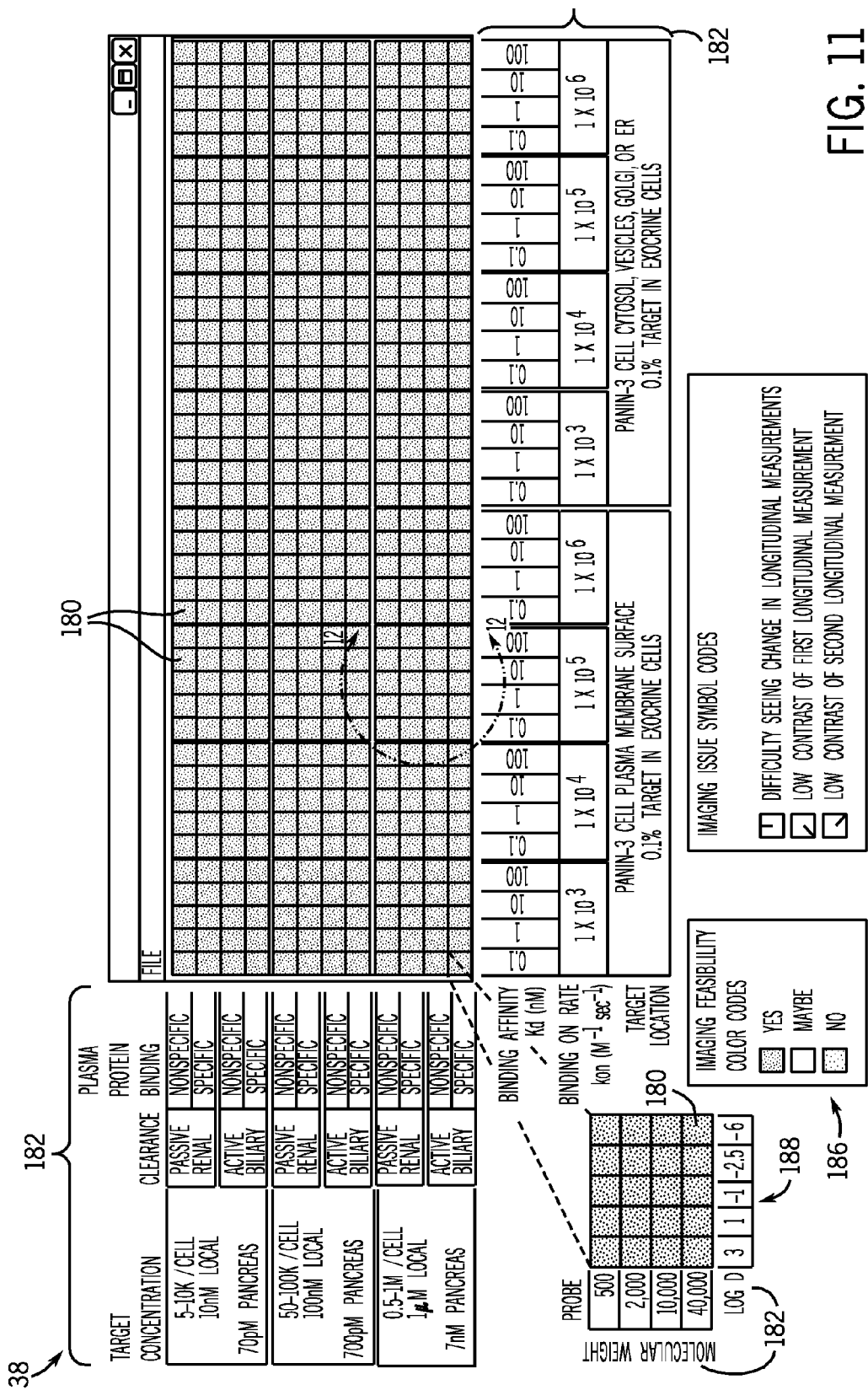
FIG. 11 depicts another imageability map, in accordance with an embodiment of the present disclosure.
Figure 12:
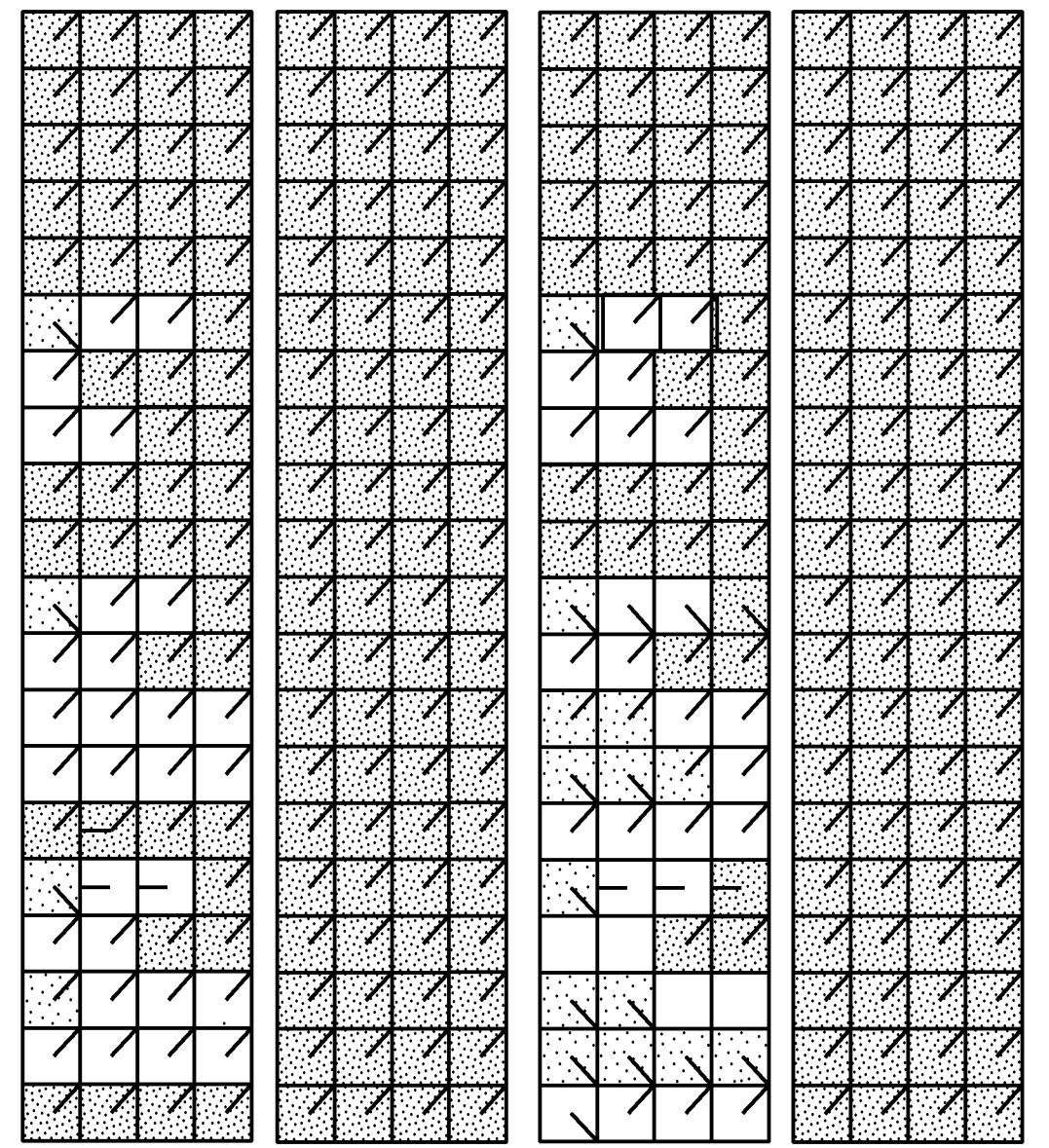
FIG. 12 depicts the inset of FIG. 11 in greater detail.

In one embodiment, the assessments of each predicted biodistribution 14 based on the scoring threshold may be aggregated and visually represented to facilitate evaluation of the different factors being reviewed and their effect on the probe being evaluated. For example, in one embodiment, a matrix or map, such as an imageability map 38, may be generated that employs a matrix distinguishing the various factors that were varied. Examples of two such imageability maps 38 are depicted in FIGS. 9 and 11, with insets of these imageability maps showing greater detail depicted in FIGS. 10 and 12 respectively.

Each small square 180 in the imageability map 38 represents a different combination of test or simulation factors 182, such as target concentration, clearance, plasma protein binding, binding affinity, binding rate, target location, probe molecular weight, and probe log D. As noted above, in certain implementations, the color of the square represents the feasibility of being able to measure a change between the healthy state and the diseased state as defined by the scoring thresholds 34. For example, a square 180 will appear green if it is feasible to measure the change, red if it is not feasible, and yellow if it might be feasible. Within each square 180 can appear small lines 184 that symbolize an imaging issue, such as difficulty seeing change in longitudinal measurements (i.e., over time), low contrast of first longitudinal measurement, low contrast of second longitudinal measurement, post/pre therapy, tumor/background, and so forth.

Referring to FIGS. 9-12, the inset legend 186 shows an enlarged representation of a 4×5 subgrids 188. In the depicted examples, each 4×5 subgrid 188 is four squares high representing four agent molecular weights of 500, 2000, 10000, and 40000 g/mole and five squares wide representing agents with five different LogD values of 3, 1, −1, −2.5, and −6. Each of these 4×5 subgrids 188 is further defined by the conditions labeled on the imageability map 38. For example, the height of the depicted imageability maps 38 includes property conditions of target concentration, clearance, and plasma protein binding. The width of the depicted imageability maps 38 include property conditions of agent-target binding affinity, binding on rate, and target location.

In this manner, an imageability map 38 may be generated that allows a reviewer to visually assess the effects of different factors on biomarker-probe performance. In particular, the imageabilty map 38 may provide an easy, intuitive, visual mechanism to assess trends or conditions associated with biomarker-probe performance or suitability. That is, if a particular biomarker-probe is suitable (or unsuitable) for use under certain conditions, this may be evidenced in the visual data, such as by the presence of clusters or trends in rows or columns of data. In this way, a particular biomarker-probe may be evaluated for usefulness in imaging or useful new biomarker-probe combinations might be suggested by the imageability map 38.

Technical effects of the invention include generating predicted bio-distributions for different biomarker-probe combinations. Some or all of the predicted biodistributions may be used to generate simulated images that can be quantitatively analyzed or scored to generate numeric thresholds for evaluating the biodistributions. The quantitative analysis of the biodistributions may be presented in a visual report, such as an imageability map, that allows simple and intuitive assessments of the biomarker-probe usefulness in imaging to be made by a reviewer.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising the steps of:
generating, on a computer, one or more biodistributions representing biomarker-probe activity using a physiological based pharmacokinetics (PBPK) model based at least on inputs of a location of a biomarker, a concentration of the biomarker, and a change in the location or concentration of the biomarker during disease progression;
generating, on a computer, one or more simulated images based on the one or more biodistributions and a digital phantom; and
quantitatively analyzing, on a computer, the one or more simulated images to derive one or more numeric classifications of biomarker-probe usefulness for imaging.

2. The method of claim 1, wherein the biodistributions comprise respective time-concentration curves or time-activity curves.

3. The method of claim 1, wherein each biodistribution corresponds to a different combination of experimental factors.

4. The method of claim 3, wherein the different combinations of experimental factors correspond to one or more of biomarker properties, probe properties, or probe dosage, simulated time frame, or probe injection location.

5. The method of claim 1, wherein generating the one or more simulated images comprises executing an imager model using one or more respective biodistributions as inputs to the imager model.

6. The method of claim 5, wherein the imager model is based on the physics of an imaging modality.

7. The method of claim 1, wherein the one or more simulated images comprise signal attributable to the respective biodistributions, signal attributable to the digital phantom, and noise attributable to an imager model used to generate the one or more simulated images.

8. The method of claim 1, wherein quantitatively analyzing the one or more simulated images comprises quantitatively assessing the ability of the biomarker-probe to distinguish an organ of interest from background tissue.

9. The method of claim 1, wherein the one or more numeric classifications comprise thresholds suitable for analyzing some of the one or more biodistributions regardless of whether simulated images are generated from the respective one or more biodistributions.

10. A method, comprising the steps of:
generating, on a computer, one or more numeric thresholds for a biomarker-probe based on simulated images, wherein each simulated image is generated using a corresponding biodistribution of a plurality of biodistributions, and the plurality of biodistributions is generated using a model that is provided inputs of a location of a biomarker, a concentration of the biomarker, and a change in the location or concentration of the biomarker during disease progression; and analyzing, on a computer, some or all of the plurality of biodistributions using the one or more numeric thresholds.

11. The method of claim 10, wherein the model is provided inputs of probe properties or physiology and anatomy parameters.

12. The method of claim 11, wherein the model comprises a physiological based pharmacokinetics (PBPK) model.

13. The method of claim 10, wherein the one or more numeric thresholds comprise at least one numeric threshold for assessing the degree to which an organ marked with the biomarker-probe is distinguishable from background tissue.

14. The method of claim 10, wherein the one or more numeric thresholds comprise at least one numeric threshold generally corresponding to a degree of noise observed in the simulated images.

15. The method of claim 10, comprising generating a matrix for the biomarker probe based upon the analysis of some or all of the plurality of biodistributions using the one or more numeric thresholds.

16. The method of claim 15, wherein the matrix comprises an imageability map comprising one or more of color or character representations.

* * * * *